(12) United States Patent
Connolly et al.

(10) Patent No.: US 7,427,625 B2
(45) Date of Patent: Sep. 23, 2008

(54) SUBSTITUTED THIATRIAZAACENAPHTHYLENE-6-CARBONITRILE KINASE INHIBITORS

(75) Inventors: Peter J. Connolly, New Providence, NJ (US); Stuart L. Emanuel, Doylestown, PA (US); Stuart Hayden, Point Pleasant, NJ (US); Sigmond G. Johnson, Flemington, NJ (US); Bharat Lagu, Hillsborough, NJ (US); Steven A. Middleton, Flemington, NJ (US); Niranjan B. Pandey, White Marsh, MD (US); Mark T. Powell, Newtown, PA (US)

(73) Assignee: Janssen Pharmaceutica, N.V. (BE)

( * ) Notice: Subject to any disclaimer, the term of this patent is extended or adjusted under 35 U.S.C. 154(b) by 0 days.

(21) Appl. No.: 11/672,177

(22) Filed: Feb. 7, 2007

(65) Prior Publication Data

US 2007/0225309 A1 Sep. 27, 2007

Related U.S. Application Data

(60) Provisional application No. 60/771,256, filed on Feb. 8, 2006.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ...................... 514/267; 544/250
(58) Field of Classification Search ................ 514/267; 544/250

See application file for complete search history.

(56) References Cited

OTHER PUBLICATIONS

Selby, Synthesis of a Novel Thiadiazacyclazine, J. Org. Chem., 53, 2386-2388 (1988).*
Klijn JG, Berns PM, Schmitz PI and Foekens JA; The clinical significance of epidermal growth factor receptor (EGF-R) in human breast cancer: a review on 5232 patients, *Endocr. Rev.*, 1992, 13, 3-17.
Salomon D and Gullick W; The erbB family of receptors and their ligands: Multiple targets for therapy, *Signal*, 2001, 2, 4-11.
Eckstrand AJ, Sugawa N, James CD and Collins VP; Amplified and rearranged epidermal growth factor receptor genes in human glioblastomas reveal deletions of sequences encoding portions of the N-and/or C-terminal tails, *Proc. Acad. Natl. Sci. USA*, 1992, 89, 4309-4313.
Wickstrand CJ, Hale LP, Batra SK, Hill ML, Humphrey PA, Kurpad SN, McLendon RE, Moscatello D, Pegram CN, Reist CJ, Traweek ST, Wong AJ, Zalutsky MR and Bigner, DD; Monoclonal antibodies against EGFRvIII are tumor specific and react with breast and lung carcinomas and malignant gliomas, *Cancer Res.*, 1995, 55, 3140-3148.

V. Koprivica, et al, EGFR activation mediates inhibition of axon regeneration by myelin and chondroitin sulfate proteoglycans, *Science*, 2005, 310, 106.
Horizons in Cancer Therapeutics: From Bench to Bedside, Signal Transduction Inhibitors, 2001, 2(2), ISSN 1532-3048.
Slamon DJ, Clark GM, Wong SG, Levin WJ, Ullrich A and McGuire WL; Human breast cancer: Correlation of relapse and survival with amplification of HER-2/neu oncogene, *Science*, 1987, 235, 177-82.
Slamon DJ, Godolphin W, Jones LA, Holt JA, Wong SG, Keith DE, et al; Studies of the HER-2/neu proto-oncogene in human breast and ovarian cancer, *Science*, 1989, 244, 707-712.
Hetzel DJ, Wilson TO, Keeney GL, Roche PC, Cha SS and Podrantz KC; HER-2/neu expression: A major prognostic factor in endometrial cancer, *Gynecol. Oncol.*, 1992, 47, 179-85.
Kirsch DG and Hochberg FH; Targeting HER-2 in brain metastases from breast cancer, *Clin. Can. Res.*, 2003, 9, 5435-5436.
Grossi PM, Ochiai H, Archer GE, McLendon RE, Zalutsky MR, Friedman AH, Friedman HS, Bigner DD and Sampson JH; Efficacy of intracerebral microinfusion of trastuzumab in an athymic rat model of intracerebral metastatic breast cancer, *Clin. Can. Res.*, 2003, 9, 5514-5520.
Wang X, et al., Epidermal growth factor receptor is a cellular receptor for juman cytomegalovirus; Nature, Jul. 24, 2003, vol. 424, 456-461.
Yeatman TJ, A renaissance for SRC, Nature, Jun. 2004, vol. 4.
Goldenberg-Furmanov, et al., Lyn is a Target Gene for Prostate Cancer Sequence-based Induces Regression of Human Tumor Xenografts; Cancer Research, Feb. 1, 2004, 64, 1058-1064.
Shah, et al., Overriding Imatinib Resistance with a Novel ABL Kinase Inhibitor, Science, Jul. 16, 2004, vol. 305, 399-401.
Donato, et al., BCR-ABL independence and LYN kinase overexpression in chronic myelogenous leukemia cells selected for resistance to STI571; Blood, Jan. 15, 2003, 101(2).
Elgemeie, G. H.; Elghandour, Ahmed H.; Elzanate, A. M.; Ahmed, S. A.; Journal of the Chemical Society, Perkin Transactions 1: Organic and Bio-Organic Chemistry (1997), (21), 3285-3290.

\* cited by examiner

*Primary Examiner*—James O. Wilson
*Assistant Examiner*—Erich A Leeser
(74) *Attorney, Agent, or Firm*—Yunling Ren

(57) ABSTRACT

The present invention is directed to substituted thiatriazaacenaphthylene-6-carbonitrile compounds of formula (I):

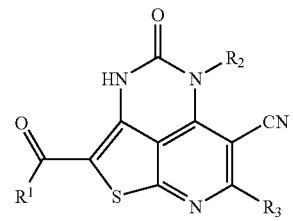

and forms thereof, their synthesis and use for treating, preventing or ameliorating a chronic or acute protein kinase mediated disease, disorder or condition.

19 Claims, No Drawings

SUBSTITUTED THIATRIAZAACENAPHTHYLENE-6-CARBONITRILE KINASE INHIBITORS

CROSS REFERENCE TO RELATED APPLICATIONS

This present application claims benefit of U.S. Provisional Patent Application Ser. No. 60/771,256, filed Feb. 8, 2006, which is incorporated herein by reference in its entirety and for all purposes.

FIELD OF THE INVENTION

The present invention is in the area of substituted thiatriazaacenaphthylene-6-carbonitrile compounds or forms thereof, their syntheses and their use as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-1 or c-MET), PDGFR ($\alpha$ and $\beta$), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (I-IV), CamKK, Chk1 and 2 (Checkpoint kinases), CKI, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 ($\alpha$ and $\beta$), PKA, P38, Erk (1-3),PKB (including all PKB subtypes) (also AKT-1, AKT-2, AKT-3 or AKT3-1), IRAK1, FRK, SGK, TAK1 or Tpl-2 (also COT).

Protein kinases play very important roles in the normal regulation of cell growth. However, as a result of dysregulation of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Defective control of protein phosphorylation due to unregulated cellular mitosis, unregulated cell proliferation and upregulated kinase activity has been implicated in a number of diseases and disease conditions, such as osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohns disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, occular diseases, viral infections, heart disease, lung or pulmonary diseases or kidney or renal diseases. Therefore, kinase inhibitors have potential use as therapeutic agents.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis.

In reference to "synovial pannus invasion in arthritis," the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface.

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

The epidermal growth factor receptor (EGFR) tyrosine-kinase family includes the receptors EGFR (also referred to as EGFR-1 or Erb-B1), HER-2 (or neu), EGFR3 and EGFR4. Epidermal Growth Factor (EGF), Transforming Growth Factor-$\alpha$ (TGF-$\alpha$) and the HER-2 ligand heregulin are three of the ligands that bind to the EGFR receptors.

EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs, such as the lungs and gastointestinal tract. The clinically prevalent cancers related to EGFR include lung, gastric and head and neck cancer (Klijn J G, Berns P M, Schmitz P I and Foekens J A; The clinical significance of epidermal growth factor receptor (EGF-R) in human breast cancer: a review on 5232 patients, *Endocr. Rev.*, 1992, 13, 3-17; Salomon D and Gullick W; The erbB family of receptors and their ligands: Multiple targets for therapy, *Signal*, 2001, 2, 4-11). Other diseases associated with increased EGFR expression include proliferative glomerulonephritis, diabetes-induced renal disease and chronic pancreatitis.

In treating cancers of the head such as brain cancers and the like, the ability of small molecule EGFR inhibitors to penetrate the blood brain barrier could have therapeutic advantages since EGFR is often overexpressed in primary brain tumors and also in breast and non-small cell lung carcinomas that frequently metastasize to the brain (Eckstrand A J, Sugawa N, James C D and Collins V P; Amplified and rearranged epidermal growth factor receptor genes in human glioblastomas reveal several deletions of sequences encoding portions of the N-and/or C-terminal tails, *Proc. Acad. Natl. Sci. USA,* 1992, 89, 4309-4313; and, Wickstrand C J, Hale L P, Batra S K, Hill M L, Humphrey P A, Kurpad S N, McLendon R E, Moscatello D, Pegram C N, Reist C J, Traweek S T, Wong A J, Zalutsky M R and Bigner, D D; Monoclonal antibodies against EGFRvIII are tumor specific and react with breast and lung carcinomas and malignant gliomas, *Cancer Res.,* 1995, 55, 3140-3148).

EGFR inhibitors tested in neurite outgrowth assays have activity in promoting neurite outgrowth in both cerebellar granule cells and dorsal root ganglion neurons, likely by acting directly on neurons to block neuronal inhibitory responses to myelin inhibitors, and thus an EGFR inhibitor may have potential use for promoting axon regeneration after brain and spinal cord injury (V. Koprivica, et al, EGFR activation mediates inhibition of axon regeneration by myelin and chondroitin sulfate proteoglycans, *Science,* 2005, 310, 106).

HER1 and HER2 overexpression has been implicated in a variety of cancers, such as bladder, breast, colorectal, endometrial, esophageal, gastric (stomach), glioma head and neck, lung (non-small cell lung cancer), ovarian, pancreatic, renal and prostate cancer.

Comparing the overexpression of HER1 and HER2 in tumors, according to order of prevalence, HER1 overexpression is found in breast, renal cell, lung, colorectal, head and neck, ovarian, pancreatic, glioma, bladder, esophageal, gastric, endometrial and cervical cancer tumors; in contrast, HER2 overexpression is found in esophageal, head and neck, lung, gastric, renal cell, breast, bladder, ovarian and colorectal, prostate and endometrial cancer tumors (Horizons in Cancer Therapeutics: From Bench to Bedside, Signal Transduction Inhibitors, 2001, 2(2), ISSN 1532-3048).

While the degree of HER2 overexpression in breast and ovarian cancer is not as great as in some other cancers, HER2 has been found to be responsible for these clinically prevalent cancers (Slamon D J, Clark G M, Wong S G, Levin W J, Ullrich A and McGuire W L; Human breast cancer: Correlation of relapse and survival with amplification of HER-2/neu oncogene, *Science,* 1987, 235, 177-82; Slamon D J, Godolphin W, Jones L A, Holt J A, Wong S G, Keith D E, et al; Studies of the HER-2/neu proto-oncogene in human breast and ovarian cancer, *Science,* 1989, 244, 707-712; Hetzel D J, Wilson T O, Keeney G L, Roche P C, Cha S S and Podrantz K C; HER-2/neu expression: A major prognostic factor in endometrial cancer, *Gynecol. Oncol.,* 1992, 47, 179-85).

Furthermore, patients with HER-2 overexpressing breast cancer frequently experience metastases to the brain (Kirsch D G and Hochberg F H; Targeting HER-2 in brain metastases from breast cancer, *Clin. Can. Res.,* 2003, 9, 5435-5436). These patients have an extremely poor prognosis and intracerebral tumors are often the cause of death. Autopsy revealed that 20-30% of patients who die of breast cancer have brain metastases (Grossi P M, Ochiai H, Archer G E, McLendon R E, Zalutsky M R, Friedman A H, Friedman H S, Bigner D D and Sampson J H; Efficacy of intracerebral microinfusion of trastuzumab in an athymic rat model of intracerebral metastatic breast cancer, *Clin. Can. Res.,* 2003, 9, 5514-5520).

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG1478 has been shown to reduce the viral load in cells that were infected in the presence of the tyrphostin (Wang X, et al., Nature, 24 Jul. 2003, Vol 424, 456-461). Accordingly, potent EGFR selective inhibitors may be useful in anti-CMV therapy.

The Src family of tyrosine-kinases includes the sub-family proteins c-Src, Lyn, Fyn, Lck, Syk, Hck, Yes, Blk, Fgr and Frk. While various members of the c-Src family are important for normal cellular proliferation, their overexpression and overactivation can promote development of cancer (Yeatman T J, Nature, June 2004, Vol. 4). For example, the Lyn kinase has been shown to be upregulated in hormone resistant prostate cancer. Tumor xenografts of hormone resistant prostate cancer cells showed delayed growth upon treatment with peptides that specifically block Lyn kinase activity (Goldenberg-Furmanov, et al., Cancer Research, 1 Feb. 2004, 64, 1058-1064).

The Lyn and Hck Src sub-family tyrosine-kinases have both been implicated in chronic myeloid leukemia (CML). CML is caused by the BCR-Abl fusion protein resulting from the t(9;22) chromosomal translocation that juxtaposes the c-Abl non-receptor tyrosine kinase gene on chromosome 9 with a breakpoint cluster region (bcr) gene on chromosome 22. The BCR-Abl fusion protein is a constitutively activated form of the Abl tyrosine kinase that drives uncontrolled growth leading to CML and many cases of adult acute lymphoblastic leukemia. Gleevec is an inhibitor of Abl that has been successfully used to treat CML. However, Gleevec does not help patients in blast crisis because they carry mutant forms of BCR-Abl that no longer bind Gleevec. Such Gleevec resistant CML cells are sensitive to a dual src/BCR-Abl inhibitor that binds and inhibits the mutant BCR-Abl and members of the src family (Shah, et al., Science, 16 Jul. 2004, Vol 305, 399-401). CML cells can also become resistant to treatment with the tyrosine kinase Abl inhibitor Gleevec in other ways. For example, CML K562 cells that become resistant to Gleevec minimize reliance on the BCR-Abl translocation for growth and instead upregulate the Lyn and Hck kinases, as demonstrated by expressing antisense Lyn in these cells, which reduced their rate of proliferation (Donato, et al., Blood, 15 Jan. 2003, 101(2)). c-Src and other Src family members are also involved in cellular adhesion, invasion and motility of tumor cells. Thus, small molecule inhibitors of the Src kinase family could offer new therapeutic opportunities for both leukemias and solid tumors.

Aurora kinases (Aurora-A, Aurora-B and Aurora-C) are highly conserved tyrosine kinases found in all organisms where they function to regulate microtubule dynamics during the M phase of the cell cycle and are essential for mitotic progression. Aurora-A kinase associates with the centrosome around the pericentriolar material, as well as the microtubules at the bipolar mitotic-spindle poles and the midbody microtubules and plays a role in spindle formation and organization of the centrosome. Aurora-B regulates chromosomal movement and cytokinesis and Aurora-C's biological function is not yet understood. The Aurora-A kinase is involved in centrosome separation, duplication and maturation as well as in bipolar spindle assembly and stability. Aurora-A is overexpressed in a number of different human cancers and tumor cell lines. Overexpression of Aurora is sufficient to induce growth in soft agar and transforms cells making them tumorigenic. Inhibition of Aurora activity results in centrosome/chromosome segregation defects leading to monopolar spindles and polyploidy which induces cell apoptosis in a variety of cancer cell lines and has suppressed tumor growth in vivo.

Angiogenesis plays a role in various processes including development of the vasculature, wound healing and maintenance of the female reproductive system. Pathological angiogenesis is associated with disease states such as cancer, diabetic retinopathy, rheumatoid arthritis, endometriosis and psoriasis. Solid-tumor cancers, in particular, are dependent on angiogenesis for their growth. The vascular endothelial growth factors (VEGFs) are mediators of both normal and pathologic angiogenesis. VEGF transmits signals into cells through their cognate receptors, which belong to the receptor tyrosine kinase (RTK) family of transmembrane receptors. These receptors are tripartite, consisting of an extracellular ligand-binding domain, a transmembrane domain, which anchors the receptor in the membrane of the cell, and an intracellular tyrosine kinase domain.

One subfamily of RTKs comprises the receptors Flt1/VEGF-R1 and KDR/Flk1/VEGF-R2, which bind VEGFs. Binding of the VEGF ligand to the receptor results in stimulation of the receptor tyrosine kinase activity and transduction of biological signals into the cell. The KDR/Flk1/VEGF-R2 receptor mediates the biological activities of mitogenesis and proliferation of endothelial cells while the Flt1/VEGF-R1 receptor mediates functions such as endothelial cell adhesion. Inhibition of KDR/Flk1/VEGF-R2 signalling has been shown to inhibit the process of angiogenesis. Inhibitors of this receptor are likely useful in controlling or limiting angiogenesis.

There is a need for potent small-molecule kinase inhibitors of one or more of the EGFR, HER-2, c-Src, Lyn, c-Abl, Aurora-A or VEGF kinase proteins and the like possessing anti-tumor cell proliferation activity, and as such are useful in treating or ameliorating a EGFR, HER-2, c-Src, Lyn, c-Abl, Aurora-A or VEGF kinase receptor mediated, angiogenesis-mediated or hyperproliferative disorder.

SUMMARY OF THE INVENTION

The present invention is directed to a compound of Formula (I):

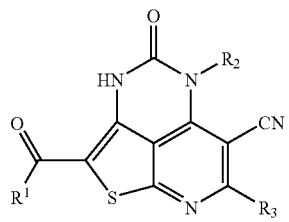

and forms thereof, wherein $R_1$, $R_2$ and $R_3$ are as defined herein.

An example of the present invention includes using a compound of formula (I) as a protein kinase inhibitor.

An example of the present invention includes a method for using a compound of formula (I) as an inhibitor of a protein kinase such as EGFR, HER-2, c-Src, Lyn, c-Abl, Aurora-A or VEGF comprising contacting the protein kinase domain or receptor with the compound.

An example of the present invention includes a method for using a compound of formula (I) and forms, pharmaceutical compositions or medicaments thereof in treating, preventing or ameliorating a kinase mediated disorder.

The present invention is further direct to a method for treating, preventing or ameliorating a chronic or acute protein kinase mediated disease, disorder or condition in a subject in need thereof comprising administering to the subject an effective amount of a compound of formula (I) or a form thereof.

These and other aspects and advantages of the invention, which will become apparent in light of the detailed description below, are achieved through use of the compounds of this invention.

DETAILED DESCRIPTION OF THE INVENTION

The present invention provides thiatriazaacenaphthylene-6-carbonitrile compounds of Formula (I):

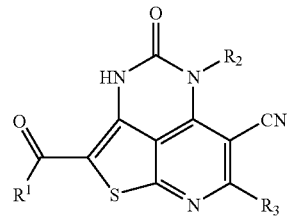

and a form thereof, wherein $R_1$ is selected from the group consisting of —N(Ra,Rb), —O(Ra) and —N(Ra)—(CH$_2$)$_p$—Ar$^1$;

Ra is selected from the group consisting of hydrogen and $C_{1-8}$alkyl;

Rb is selected from the group consisting of hydrogen, $C_{1-8}$alkyl and hydroxy-($C_{1-8}$)alkyl;

alternatively, when $R_1$ is —N(Ra,Rb), then Ra and Rb may be taken together with the nitrogen of attachment to form a heterocyclyl ring having at least one said nitrogen atom, wherein said ring is optionally substituted with one, two or three substituents each selected from the group consisting of $C_{1-8}$alkyl, $C_{2-8}$alkenyl, $C_{2-8}$alkynyl, $C_{1-8}$alkoxy, halogen, hydroxy, hydroxy-($C_{1-8}$)alkyl, hydroxy-($C_{1-8}$)alkoxy, amino and $C_{1-8}$alkyl-amino;

p is 0, 1, 2, 3 or 4;

Ar$^1$ is selected from the group consisting of aryl, heteroaryl, benzofused heteroaryl, heterocyclyl and benzofused heterocyclyl each optionally substituted with one, two or three substituents each selected from the group consisting of $R_4$—($C_{1-8}$)alkyl, $R_4$—($C_{2-8}$)alkenyl, $R_4$—($C_{2-8}$)alkynyl, $R_4$—($C_{1-8}$)alkoxy, cyano, halogen, nitro, halo-($C_{1-8}$)alkyl, halo-($C_{1-8}$)alkoxy, hydroxy, hydroxy-($C_{1-8}$)alkyl, hydroxy-($C_{1-8}$)alkoxy, $C_{1-8}$alkoxy-carbonyl, $C_{1-8}$alkoxy-carbonyl-amino, amino-($C_{1-8}$)alkyl, $C_{1-8}$alkyl-amino-($C_{1-8}$)alkyl, amino, $C_{1-8}$alkyl-amino, $C_{3-8}$cycloalkyl-amino, heterocyclyl-amino (optionally substituted on heterocyclyl with one or two $C_{1-8}$alkyl substituents) and heterocyclyl-($C_{1-8}$)alkyl-amino (optionally substituted on heterocyclyl with one or two $C_{1-8}$alkyl substituents);

$R_4$ is hydrogen or is one, two or three substituents each selected from the group consisting of $C_{3-8}$cycloalkyl, aryl, heteroaryl and heterocyclyl each optionally substituted with one, two or three substituents each selected from the group consisting of $C_{1-8}$alkyl, $C_{1-8}$alkoxy, $C_{1-8}$alkoxy-($C_{1-8}$)alkyl, cyano, halogen, hydroxy, halo-($C_{1-8}$)alkyl, halo-($C_{1-8}$)alkoxy, hydroxy-($C_{1-8}$)alkyl, hydroxy-($C_{1-8}$)alkoxy, $C_{1-8}$alkoxy-carbonyl, amino-($C_{1-8}$)alkyl, $C_{1-8}$alkyl-amino-($C_{1-8}$)alkyl, amino, $C_{1-8}$alkyl-amino, $C_{1-8}$alkoxy-carbonyl-amino;

$R_2$ is selected from the group consisting of aryl, heteroaryl, benzofused heteroaryl, heterocyclyl and benzofused heterocyclyl each optionally substituted with one, two or three substituents each selected from the group consisting of $C_{1-8}$alkyl, $C_{2-8}$alkenyl, $C_{2-8}$alkynyl, $C_{1-8}$alkoxy, cyano, halogen, halo-($C_{1-8}$)alkyl, halo-($C_{1-8}$)alkoxy, hydroxy, heteroaryl-oxy, aryl-oxy (optionally substituted on heteroaryl and aryl with one, two or three substituents each selected from the group consisting of $C_{1-8}$alkyl, $C_{1-8}$alkoxy and halogen); and $R_3$ is hydrogen or is selected from the group consisting of $R_4$—($C_{1-8}$)alkyl, $R_4$—($C_{2-8}$)alkenyl, $R_4$—($C_{2-8}$)alkynyl, halogen, hydroxy, $C_3$-cycloalkyl, heteroaryl, aryl and heterocyclyl, optionally substituted on heteroaryl and aryl with one, two or three substituents each selected from the group consisting of $C_{1-8}$alkyl, $C_{1-8}$alkoxy and halogen.

An example of the present invention is a compound of Formula (I) and a form thereof wherein $R_1$ is —N(Ra,Rb).

An example of the present invention is a compound of Formula (I) and a form thereof wherein $R_1$ is —O(Ra).

An example of the present invention is a compound of Formula (I) and a form thereof wherein $R_1$ is —N(Ra)—(CH$_2$)$_p$—Ar$^1$.

An example of the present invention is a compound of Formula (I) and a form thereof wherein Ra is hydrogen.

An example of the present invention is a compound of Formula (I) and a form thereof wherein Ra is $C_{1-8}$alkyl.

An example of the present invention is a compound of Formula (I) and a form thereof wherein Rb is selected from the group consisting of hydrogen and hydroxy-($C_{1-8}$)alkyl.

An example of the present invention is a compound of Formula (I) and a form thereof wherein, when $R_1$ is —N(Ra, Rb), then Ra and Rb may be taken together with the nitrogen of attachment to form a heterocyclyl ring having at least one said nitrogen atom, wherein said ring is optionally substituted with one substituent selected from the group consisting of $C_{1-8}$alkyl, halogen, hydroxy, hydroxy-($C_{1-8}$)alkyl, amino and $C_{1-8}$alkyl-amino.

An example of the present invention is a compound of Formula (I) and a form thereof wherein p is 0, 1 or 2.

An example of the present invention is a compound of Formula (I) and a form thereof wherein Ar$^1$ is selected from the group consisting of aryl, heteroaryl and heterocyclyl each optionally substituted with one or two substituents each selected from the group consisting of $R_4$—($C_{1-8}$)alkyl, $R_4$—($C_{1-8}$)alkoxy, cyano, halogen, nitro, halo-($C_{1-8}$)alkyl, halo-($C_{1-8}$)alkoxy, hydroxy, hydroxy-($C_{1-8}$)alkyl, hydroxy-($C_{1-8}$)alkoxy, $C_{1-8}$alkoxy-carbonyl, $C_{1-8}$alkoxy-carbonyl-amino, amino-($C_{1-8}$)alkyl, $C_{1-8}$alkyl-amino-($C_{1-8}$)alkyl, amino, $C_{1-8}$alkyl-amino and heterocyclyl-($C_{1-8}$)alkyl-amino.

An example of the present invention is a compound of Formula (I) and a form thereof wherein Ar$^1$ is selected from the group consisting of aryl, heteroaryl and heterocyclyl each optionally substituted with one or two substituents each selected from the group consisting of $R_4$—($C_{1-8}$)alkyl, $R_4$—($C_{1-8}$)alkoxy, $C_{1-8}$alkyl-amino and heterocyclyl-($C_{1-8}$)alkyl-amino.

An example of the present invention is a compound of Formula (I) and a form thereof wherein $R_4$ is hydrogen or is one, two or three substituents each selected from the group consisting of aryl, heteroaryl and heterocyclyl each optionally substituted with one or two substituents each selected from the group consisting of $C_{1-8}$alkyl, $C_{1-8}$alkoxy, halogen, hydroxy, halo-($C_{1-8}$)alkyl, halo-($C_{1-8}$)alkoxy, hydroxy-($C_{1-8}$)alkyl, hydroxy-($C_{1-8}$)alkoxy, amino-($C_{1-8}$)alkyl, $C_{1-8}$alkyl-amino-($C_{1-8}$)alkyl, amino, $C_{1-8}$alkyl-amino and $C_{1-8}$alkoxy-carbonyl-amino.

An example of the present invention is a compound of Formula (I) and a form thereof wherein $R_4$ is hydrogen or is heterocyclyl optionally substituted with one or two substituents each selected from the group consisting of $C_{1-8}$alkoxy, halogen, hydroxy, hydroxy-($C_{1-8}$)alkyl, amino, $C_{1-8}$alkyl-amino and $C_{1-8}$alkoxy-carbonyl-amino.

An example of the present invention is a compound of Formula (I) and a form thereof wherein Ar$^1$ is selected from the group consisting of aryl, heteroaryl and heterocyclyl each optionally substituted with one or two substituents each selected from the group consisting of $R_4$—($C_{1-8}$)alkyl, $R_4$—($C_{1-8}$)alkoxy, cyano, halogen, nitro, halo-($C_{1-8}$)alkyl, halo-($C_{1-8}$)alkoxy, hydroxy, hydroxy-($C_{1-8}$)alkyl, hydroxy-($C_{1-8}$)alkoxy, $C_{1-8}$alkoxy-carbonyl, $C_{1-8}$alkoxy-carbonyl-amino, amino-($C_{1-8}$)alkyl, $C_{1-8}$alkyl-amino-($C_{1-8}$)alkyl, amino, $C_{1-8}$alkyl-amino and heterocyclyl-($C_{1-8}$)alkyl-amino; and $R_4$ is hydrogen or is one, two or three substituents each selected from the group consisting of aryl, heteroaryl and heterocyclyl each optionally substituted with one or two substituents each selected from the group consisting of $C_{1-8}$alkyl, $C_{1-8}$alkoxy, halogen, hydroxy, halo-($C_{1-8}$)alkyl, halo-($C_{1-8}$)alkoxy, hydroxy-($C_{1-8}$)alkyl, hydroxy-($C_{1-8}$)alkoxy, amino-($C_{1-8}$)alkyl, $C_{1-8}$alkyl-amino-($C_{1-8}$)alkyl, amino, $C_{1-8}$alkyl-amino and $C_{1-8}$alkoxy-carbonyl-amino.

An example of the present invention is a compound of Formula (I) and a form thereof wherein Ar$^1$ is selected from the group consisting of aryl, heteroaryl and heterocyclyl each optionally substituted with one or two substituents each selected from the group consisting of $R_4$—($C_{1-8}$)alkyl, $R_4$—($C_{1-8}$)alkoxy, $C_{1-8}$alkyl-amino and heterocyclyl-($C_{1-8}$)alkyl-amino; and $R_4$ is hydrogen or is heterocyclyl optionally substituted with one or two substituents each selected from the group consisting of $C_{1-8}$alkyl, $C_{1-8}$alkoxy, halogen, hydroxy, hydroxy-($C_{1-8}$)alkyl, amino, $C_{1-8}$alkyl-amino and $C_{1-8}$alkoxy-carbonyl-amino.

An example of the present invention is a compound of Formula (I) and a form thereof wherein $R_2$ is selected from the group consisting of aryl, heteroaryl and benzofused heterocyclyl each optionally substituted with one, two or three substituents each selected from the group consisting of $C_{1-8}$alkyl, $C_{1-8}$alkoxy, halogen, halo-($C_{1-8}$)alkyl, halo-($C_{1-8}$)alkoxy, heteroaryl-oxy, aryl-oxy (optionally substituted on heteroaryl and aryl with one, two or three substituents each selected from the group consisting of $C_{1-8}$alkyl, $C_{1-8}$alkoxy and halogen).

An example of the present invention is a compound of Formula (I) and a form thereof wherein $R_2$ is selected from the group consisting of aryl, heteroaryl and benzofused heterocyclyl each optionally substituted with one, two or three substituents each selected from the group consisting of $C_{1-8}$alkoxy, halogen and aryl-oxy.

An example of the present invention is a compound of Formula (I) and a form thereof wherein $R_3$ is hydrogen or is selected from the group consisting of $R_4$—($C_{1-8}$)alkyl, $R_4$—($C_{2-8}$)alkenyl, $R_4$—($C_{2-8}$)alkynyl, halogen, hydroxy, $C_3$-cycloalkyl, heteroaryl, aryl and heterocyclyl, optionally substituted on heteroaryl and aryl with one, two or three substituents each selected from the group consisting of $C_{1-8}$alkyl, $C_{1-8}$alkoxy and halogen.

An example of the present invention is a compound of Formula (I) and a form thereof wherein $R_3$ is hydrogen or is selected from the group consisting of $C_{1-8}$alkyl, halogen, hydroxy, aryl and heterocyclyl, optionally substituted on aryl with one or two halogen substituents.

An example of the present invention is a compound of Formula (I) and a form thereof wherein $R_1$ is selected from the group consisting of —N(Ra,Rb), —O(Ra) and —N(Ra)—(CH$_2$)$_p$—Ar$^1$;

Ra is selected from the group consisting of hydrogen and $C_{1-8}$alkyl;

Rb is selected from the group consisting of hydrogen and hydroxy($C_{1-8}$)alkyl;

alternatively, when $R_1$ is —N(Ra,Rb), then Ra and Rb may be taken together with the nitrogen of attachment to form a heterocyclyl ring having at least one said nitrogen atom, wherein said ring is optionally substituted with one substituent selected from the group consisting of $C_{1-8}$alkyl, halogen, hydroxy, hydroxy-($C_{1-8}$)alkyl, amino and $C_{1-8}$alkyl-amino;

p is 0, 1 or 2;

Ar$^1$ is selected from the group consisting of aryl, heteroaryl and heterocyclyl each optionally substituted with one or two substituents each selected from the group consisting of $R_4$—($C_{1-8}$)alkyl, $R_4$—($C_{1-8}$)alkoxy, $C_{1-8}$alkyl-amino and heterocyclyl-($C_{1-8}$)alkyl-amino;

$R_4$ is hydrogen or is heterocyclyl optionally substituted with one or two substituents each selected from the group consisting of $C_{1-8}$alkyl, $C_{1-8}$alkoxy, halogen, hydroxy, hydroxy-($C_{1-8}$)alkyl, amino, $C_{1-8}$alkyl-amino and $C_{1-8}$alkoxy-carbonyl-amino;

$R_2$ is selected from the group consisting of aryl, heteroaryl and benzofused heterocyclyl each optionally substituted with one, two or three substituents each selected from the group consisting of $C_{1-8}$alkoxy, halogen and aryl-oxy; and $R_3$ is hydrogen or is selected from the group consisting of $C_{1-8}$alkyl, halogen, hydroxy, aryl and heterocyclyl, optionally substituted on aryl with one or two halogen substituents.

An example of the present invention is a compound of Formula (I) and a form thereof, wherein $R_1$, $R_2$ and $R_3$ is selected from:

| Cpd | $R_1$ | $R_2$ | $R_3$ |
| --- | --- | --- | --- |
| 1 | OCH$_2$CH$_3$ | 3-Cl-phenyl | OH |
| 2 | NH-(4-CH$_2$-piperidin-1-yl)-phenyl | 3-Cl-phenyl | H |
| 3 | NH-(4-CH$_2$-morpholin-4-yl)-phenyl | 3-Cl-phenyl | H |
| 4 | NH-(4-CH$_2$-morpholin-4-yl)-phenyl | 5-Cl-benzo[1,3]dioxol-4-yl | H |
| 5 | NH-(4-CH$_2$-morpholin-4-yl)-phenyl | 2,4-Cl$_2$-5-OCH$_3$-phenyl | H |
| 6 | NH-[4-(CH$_2$)$_2$-morpholin-4-yl]-phenyl | 2,4-Cl$_2$-5-OCH$_3$-phenyl | H |
| 7 | OCH$_2$CH$_3$ | 5-Cl-benzo[1,3]dioxol-4-yl | morpholin-4-yl |
| 8 | NH-(4-CH$_2$-morpholin-4-yl)-phenyl | 5-Cl-benzo[1,3]dioxol-4-yl | morpholin-4-yl |
| 9 | NH-(4-CH$_2$-morpholin-4-yl)-phenyl | 5-Cl-benzo[1,3]dioxol-4-yl | CH$_3$ |
| 10 | NH-(1-CH$_3$)-piperidin-4-yl | 5-Cl-benzo[1,3]dioxol-4-yl | H |
| 11 | NH-[4-(CH$_2$)$_2$-piperidin-1-yl]-phenyl | 5-Cl-benzo[1,3]dioxol-4-yl | H |
| 12 | NH-[4-(CH$_2$)$_2$-(4-CH$_3$-piperazin-1-yl)]-phenyl | 5-Cl-benzo[1,3]dioxol-4-yl | H |
| 13 | NH-[4-(CH$_2$)$_2$-morpholin-4-yl]-phenyl | 5-Cl-benzo[1,3]dioxol-4-yl | H |
| 14 | OCH$_2$CH$_3$ | pyridin-4-yl | OH |
| 15 | OCH$_2$CH$_3$ | pyridin-4-yl | 2-Cl-5-F-phenyl |
| 16 | NH—(CH$_2$)$_2$-pyrrolidin-1-yl | pyridin-4-yl | 2-Cl-5-F-phenyl |
| 17 | OCH$_2$CH$_3$ | 5-Cl-benzo[1,3]dioxol-4-yl | H |
| 18 | NH-[4-CH$_2$-(4-OCH$_3$-piperidin-1-yl)]-phenyl | 5-Cl-benzo[1,3]dioxol-4-yl | H |
| 19 | NH-[4-CH$_2$-(4-CH$_3$-piperidin-1-yl)]-phenyl | 5-Cl-benzo[1,3]dioxol-4-yl | H |
| 20 | NH-[4-CH$_2$-(3-CH$_2$OH-piperidin-1-yl)]-phenyl | 5-Cl-benzo[1,3]dioxol-4-yl | H |
| 21 | 3-CH$_2$OH-piperidin-1-yl | 5-Cl-benzo[1,3]dioxol-4-yl | H |
| 22 | NH-[4-CH$_2$-(4-CH$_2$OH-piperidin-1-yl)]-phenyl | 5-Cl-benzo[1,3]dioxol-4-yl | H |
| 23 | NH-[4-CH$_2$-(4-OH-piperidin-1-yl)]-phenyl | 5-Cl-benzo[1,3]dioxol-4-yl | H |
| 24 | NH-{4-CH$_2$-[3,5-(CH$_3$)$_2$-morpholin-4-yl]}-phenyl | 5-Cl-benzo[1,3]dioxol-4-yl | H |
| 25 | NH-{4-CH$_2$-[2,6-cis-(CH$_3$)$_2$-morpholin-4-yl]}-phenyl | 5-Cl-benzo[1,3]dioxol-4-yl | H |

-continued

| Cpd | R₁ | R₂ | R₃ |
|---|---|---|---|
| 26 | NH-[4-CH$_2$-(4-F-piperidin-1-yl)]-phenyl | 5-Cl-benzo[1,3]dioxol-4-yl | H |
| 27 | NH-[3-N(CH$_3$)$_2$-4-CH$_2$-morpholin-4-yl]-phenyl | 5-Cl-benzo[1,3]dioxol-4-yl | H |
| 28 | 4-OH-piperidin-1-yl | 5-Cl-benzo[1,3]dioxol-4-yl | H |
| 29 | N(CH$_3$)-(4-CH$_2$-morpholin-4-yl)-phenyl | 5-Cl-benzo[1,3]dioxol-4-yl | H |
| 30 | NH-[6-NH(CH$_2$)$_3$-morpholin-4-yl]-pyridin-3-yl | 5-Cl-benzo[1,3]dioxol-4-yl | H |
| 31 | NH-[3-OCH$_3$-4-O(CH$_2$)$_2$-piperidin-1-yl]-phenyl | 5-Cl-benzo[1,3]dioxol-4-yl | H |
| 32 | NH-[4-OCH$_2$-(1-CH$_3$-piperidin-2-yl)]-phenyl | 5-Cl-benzo[1,3]dioxol-4-yl | H |
| 33 | NH-pyrazol-3-yl | 5-Cl-benzo[1,3]dioxol-4-yl | H |
| 34 | NH-(5-CH$_3$)-isoxazol-3-yl | 5-Cl-benzo[1,3]dioxol-4-yl | H |
| 35 | NH-pyrimidin-2-yl | 5-Cl-benzo[1,3]dioxol-4-yl | H |
| 36 | NH-pyridin-3-yl | 5-Cl-benzo[1,3]dioxol-4-yl | H |
| 37 | NH-pyridin-2-yl | 5-Cl-benzo[1,3]dioxol-4-yl | H |
| 38 | NH—C(CH$_3$)$_2$CH$_2$OH | 5-Cl-benzo[1,3]dioxol-4-yl | H |
| 39 | NH-(1-CH$_3$)-pyrazol-3-yl | 5-Cl-benzo[1,3]dioxol-4-yl | H |
| 40 | NH-pyridin-4-yl | 5-Cl-benzo[1,3]dioxol-4-yl | H |
| 41 | 4-N(CH$_3$)$_2$-piperidin-1-yl | 5-Cl-benzo[1,3]dioxol-4-yl | H |
| 42 | NH-{4-CH$_2$-[4-N(CH$_3$)$_2$-piperidin-1-yl]}-phenyl | 5-Cl-benzo[1,3]dioxol-4-yl | H |
| 43 | 3-F-piperidin-1-yl | 5-Cl-benzo[1,3]dioxol-4-yl | H |
| 44 | NH-[4-CH$_2$-(3-F-piperidin-1-yl)]-phenyl | 5-Cl-benzo[1,3]dioxol-4-yl | H |
| 45 | NH-[3-OCH$_3$-4-CH$_2$-morpholin-4-yl]-phenyl | 4-phenoxy-phenyl | H |
| 46 | NH-{4-CH$_2$-[4-NHC(O)OC(CH$_3$)$_3$-piperidin-1-yl]}-phenyl | 5-Cl-benzo[1,3]dioxol-4-yl | H |
| 47 | NH-[4-CH$_2$-(4-NH$_2$-piperidin-1-yl)]-phenyl | 5-Cl-benzo[1,3]dioxol-4-yl | H |
| 48 | NH-[4-(CH$_2$)$_2$-piperidin-1-yl]-phenyl | 4-phenoxy-phenyl | H |
| 49 | NH-(4-CH$_2$-piperidin-1-yl)-phenyl | 4-phenoxy-phenyl | H |
| 50 | NH-(4-CH$_2$-morpholin-4-yl)-phenyl | 4-phenoxy-phenyl | H |
| 51 | NH-[4-CH$_2$-(4-OCH$_3$-piperidin-1-yl)]-phenyl | 4-phenoxy-phenyl | H |
| 52 | OCH$_2$CH$_3$ | 4-phenoxy-phenyl | OH |
| 53 | OCH$_2$CH$_3$ | 4-phenoxy-phenyl | Cl |
| 54 | NH-[4-CH$_2$-(4,4-F$_2$-piperidin-1-yl)]-phenyl | 5-Cl-benzo[1,3]dioxol-4-yl | H |

An example of the present invention is a compound of Formula (I) and a form thereof, wherein $R_1$ is selected from OCH$_2$CH$_3$, NH-(4-CH$_2$-piperidin-1-yl)-phenyl, NH-(4-CH$_2$-morpholin-4-yl)-phenyl, NH-[4-(CH$_2$)$_2$-morpholin-4-yl]-phenyl, NH-(1-CH$_3$)-piperidin-4-yl, NH-[4-(CH$_2$)$_2$-piperidin-1-yl]-phenyl, NH-[4-(CH$_2$)$_2$-(4-CH$_3$-piperazin-1-yl)]-phenyl, NH-(CH$_2$)$_2$-pyrrolidin-1-yl, NH-[4-CH$_2$-(4-OCH$_3$-piperidin-1-yl)]-phenyl, NH-[4-CH$_2$-(4-CH$_3$-piperidin-1-yl)]-phenyl, NH-[4-CH$_2$-(3-CH$_2$OH-piperidin-1-yl)]-phenyl, 3-CH$_2$OH-piperidin-1-yl, NH-[4-CH$_2$-(4-CH$_2$OH-piperidin-1-yl)]-phenyl, NH-[4-CH$_2$-(4-OH-piperidin-1-yl)]-phenyl, NH-{4-CH$_2$-[3,5-(CH$_3$)$_2$-morpholin-4-yl]}-phenyl, NH-{4-CH$_2$-[2,6-cis-(CH$_3$)$_2$-morpholin-4-yl]}-phenyl, NH-[4-CH$_2$-(4-F-piperidin-1-yl)]-phenyl, NH-[3-N(CH$_3$)$_2$-4-CH$_2$-morpholin-4-yl]-phenyl, 4-OH-piperidin-1-yl, N(CH$_3$)-(4-CH$_2$-morpholin-4-yl)-phenyl, NH-[6-NH(CH$_2$)$_3$-morpholin-4-yl]-pyridin-3-yl, NH-[3-OCH$_3$-4-O(CH$_2$)$_2$-piperidin-1-yl]-phenyl, NH-[4-OCH$_2$-(1-CH$_3$-piperidin-2-yl)]-phenyl, NH-pyrazol-3-yl, NH-(5-CH$_3$)-isoxazol-3-yl, NH-pyrimidin-2-yl, NH-pyridin-3-yl, NH-pyridin-2-yl, NH—C(CH$_3$)$_2$CH$_2$OH, NH-(1-CH$_3$)-pyrazol-3-yl, NH-pyridin-4-yl, 4-N(CH$_3$)$_2$-piperidin-1-yl, NH-{4-CH$_2$-[4-N(CH$_3$)$_2$-piperidin-1-yl]}-phenyl, 3-F-piperidin-1-yl, NH-[4-CH$_2$-(3-F-piperidin-1-yl)]-phenyl, NH-[3-OCH$_3$-4-CH$_2$-morpholin-4-yl]-phenyl, NH-{4-CH$_2$-[4-NHC(O)OC(CH$_3$)$_3$-piperidin-1-yl]}-phenyl, NH-[4-CH$_2$-(4-NH$_2$-piperidin-1-yl)]-phenyl or NH-[4-CH$_2$-(4,4-F$_2$-piperidin-1-yl)]-phenyl;

$R_2$ is selected from 3-Cl-phenyl, 2,4-Cl$_2$-5-OCH$_3$-phenyl, pyridin-4-yl, 4-phenoxy-phenyl or 5-Cl-benzo[1,3]dioxol-4-yl; and $R_3$ is selected from hydrogen, OH, Cl, morpholin-4-yl, CH$_3$ or 2-Cl-5-F-phenyl.

Compounds representative of a compound of Formula (I) or a form thereof include compounds and forms thereof selected from:

Cpd 1
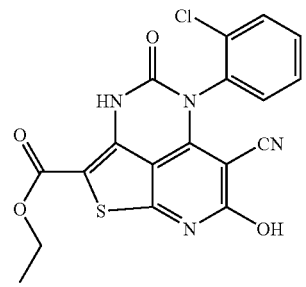
Cpd 2
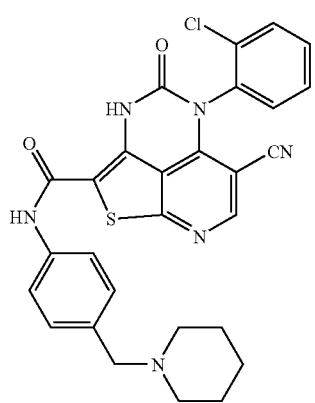
Cpd 3
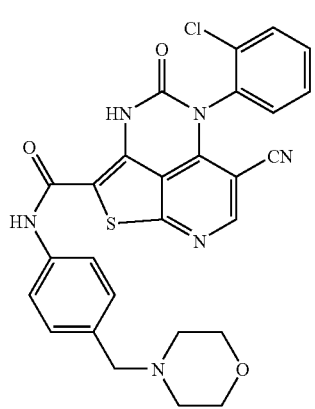
-continued
Cpd 4
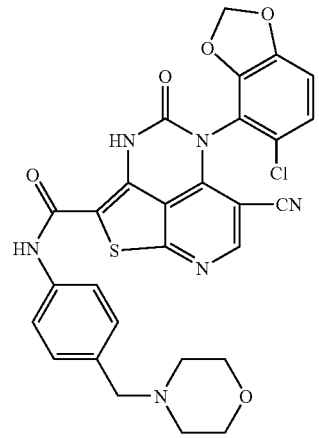
Cpd 5
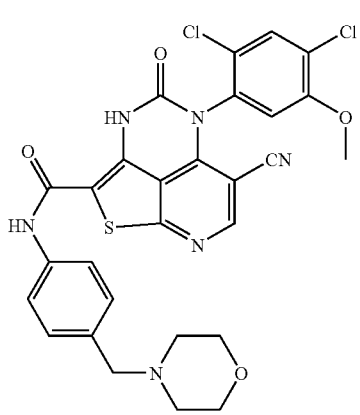
Cpd 6
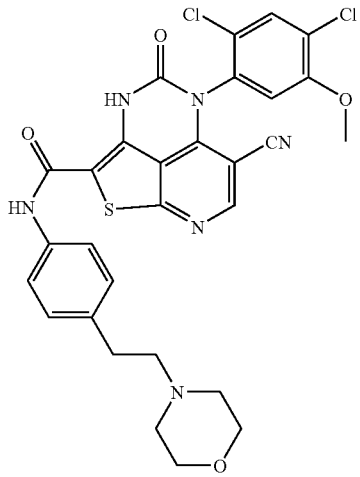
Cpd 7
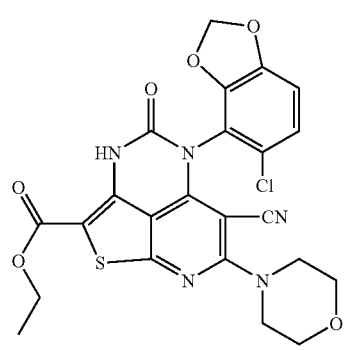

Cpd 8
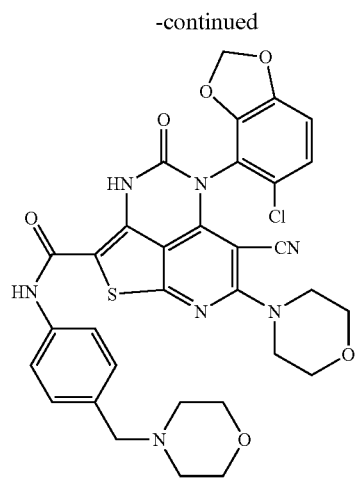
Cpd 9
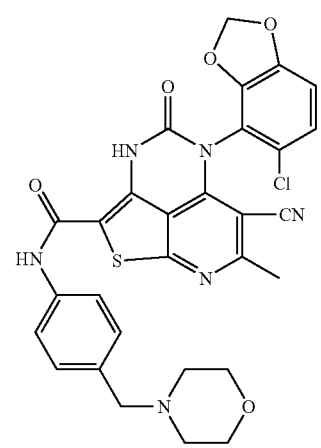
Cpd 10
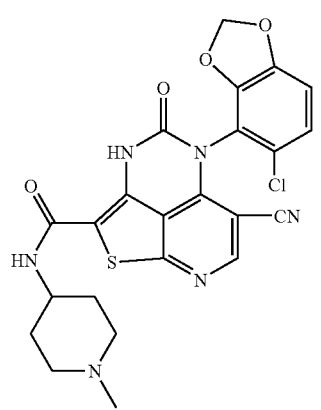
Cpd 11
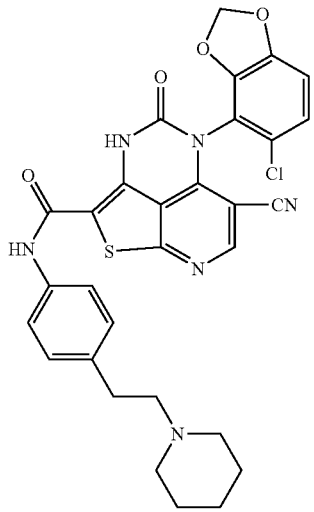
Cpd 12
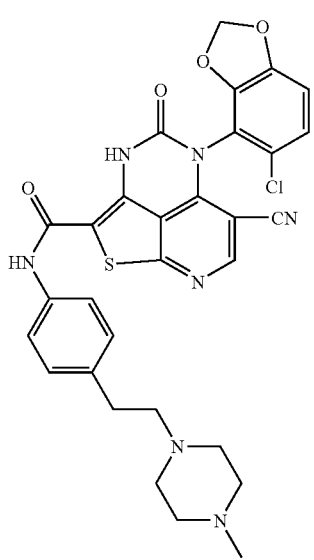

-continued
Cpd 13
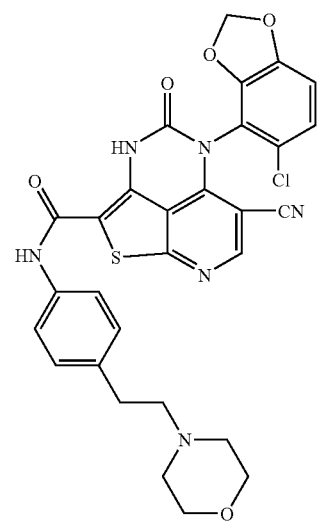
Cpd 14
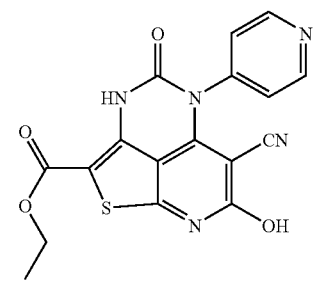
Cpd 15
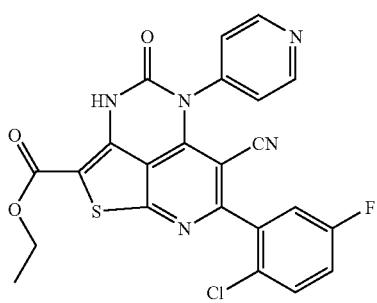
-continued
Cpd 16
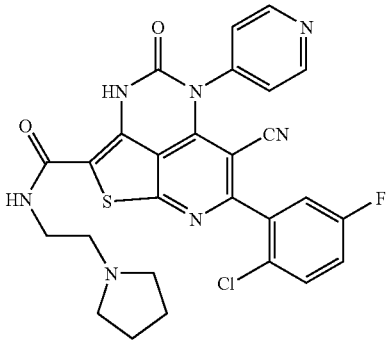
Cpd 17
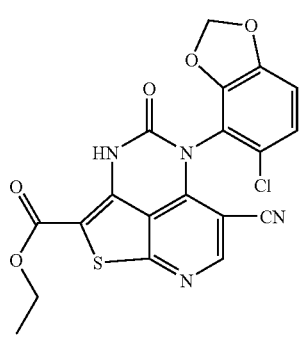
Cpd 18
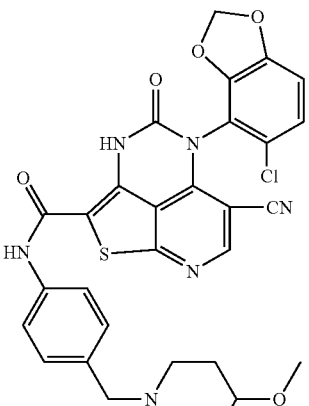
Cpd 19
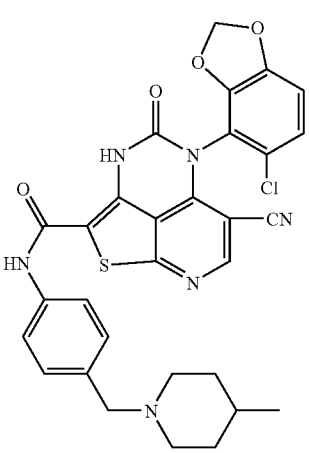

-continued
Cpd 20
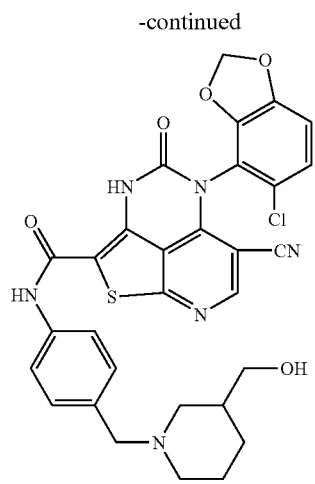
Cpd 21
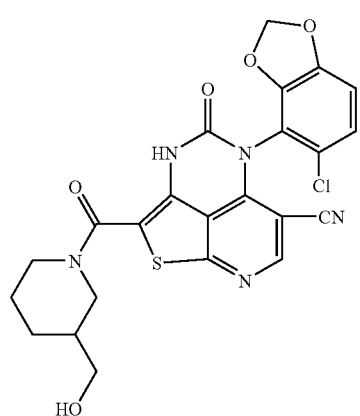
Cpd 22
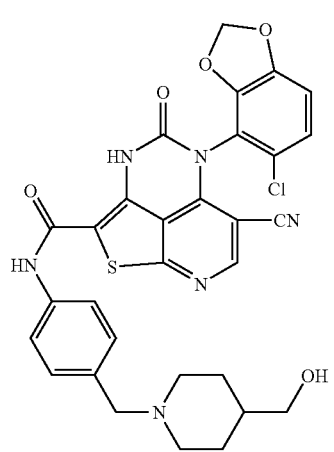
-continued
Cpd 23
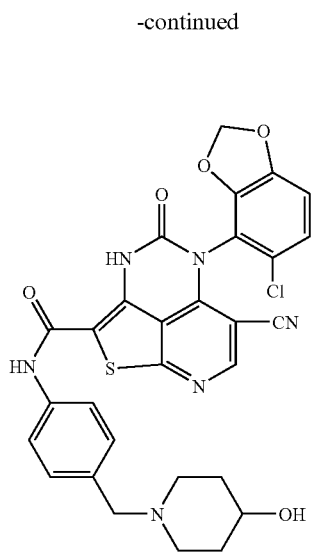
Cpd 24
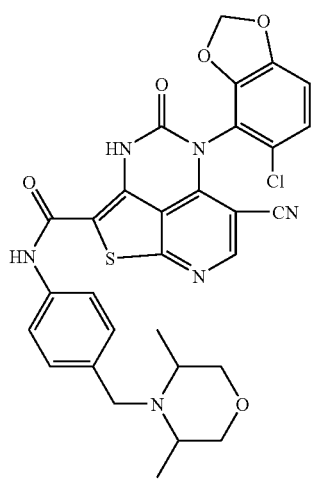

Cpd 25
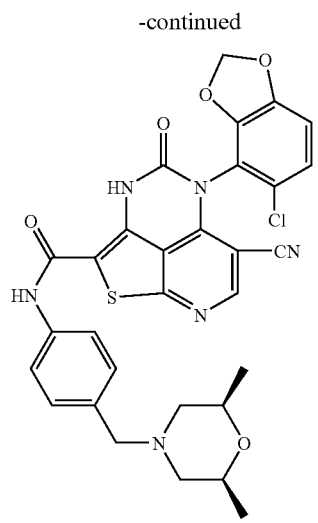
Cpd 26
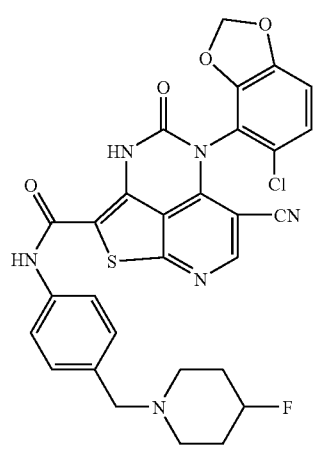
Cpd 27
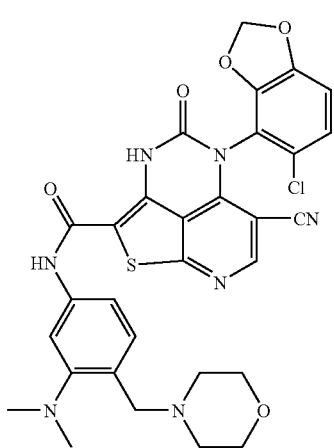
Cpd 28
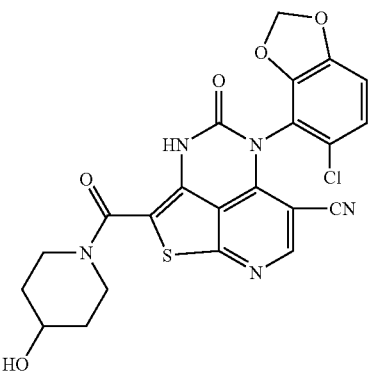
Cpd 29

-continued
Cpd 30
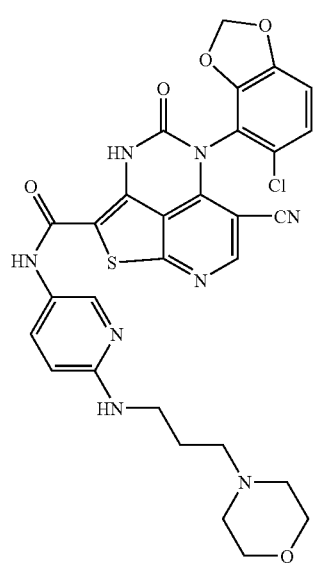
Cpd 31
Cpd 32
Cpd 33
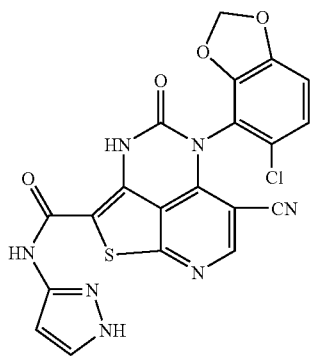
Cpd 34
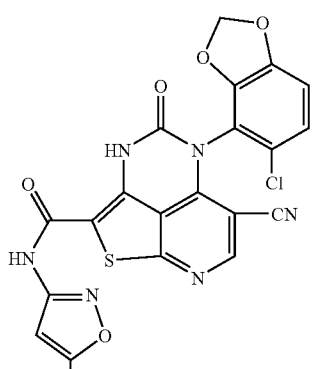
Cpd 35
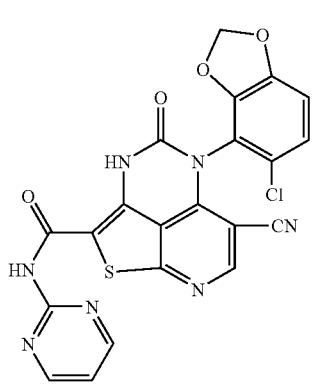
Cpd 36
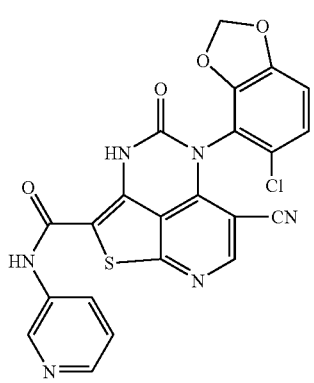

-continued
Cpd 37
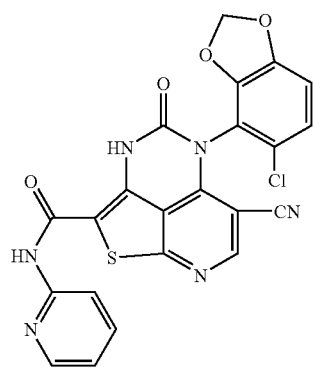
Cpd 38
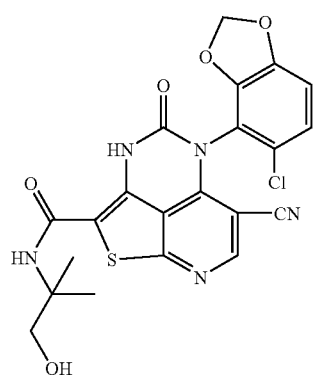
Cpd 39
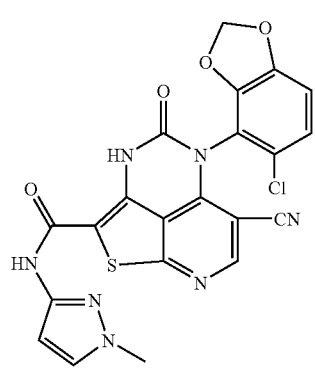
Cpd 40
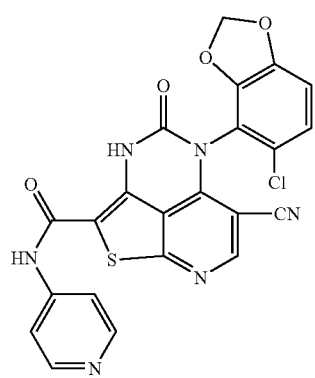
-continued
Cpd 41
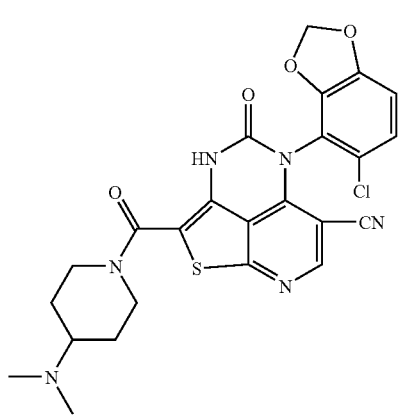
Cpd 42
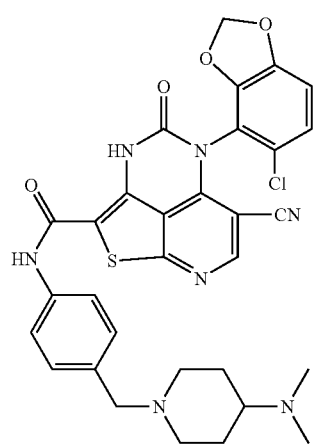
Cpd 43
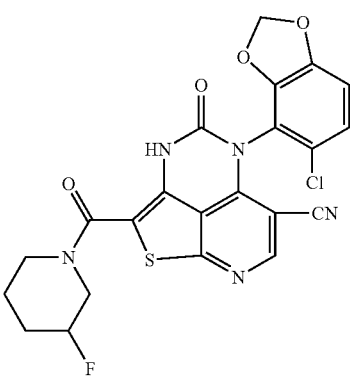

-continued
Cpd 44
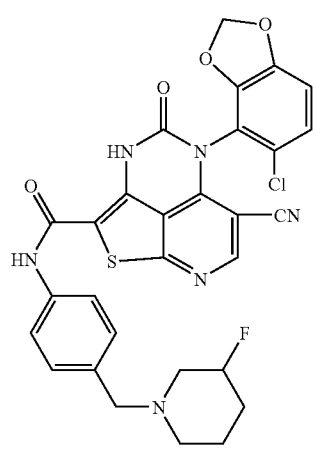
Cpd 45
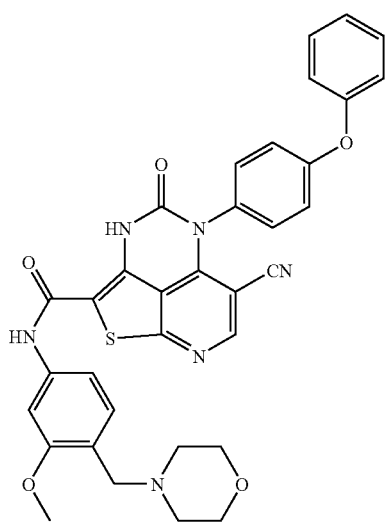
Cpd 46
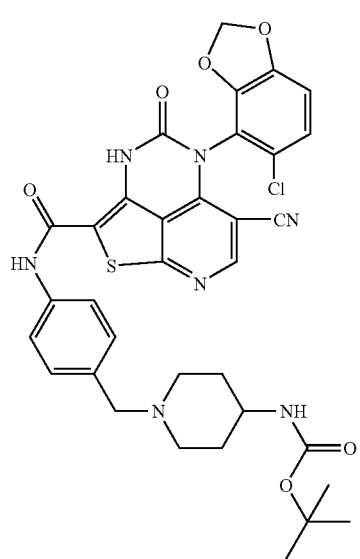
Cpd 47
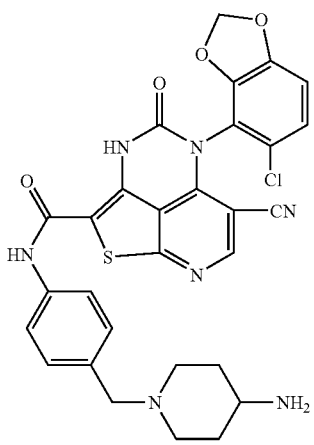
Cpd 48
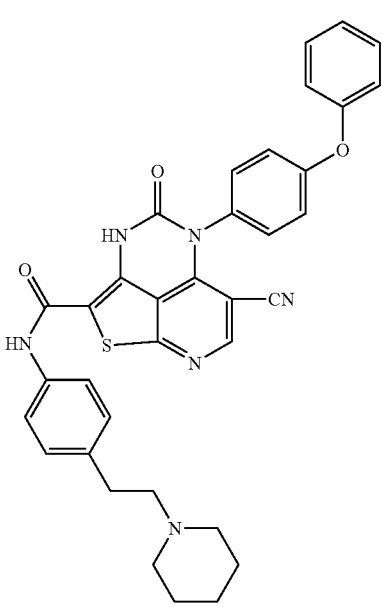

-continued

Cpd 49
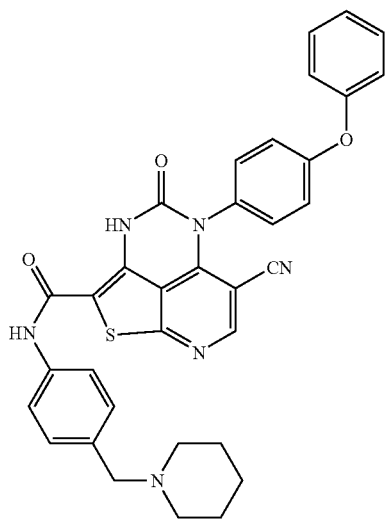

Cpd 50
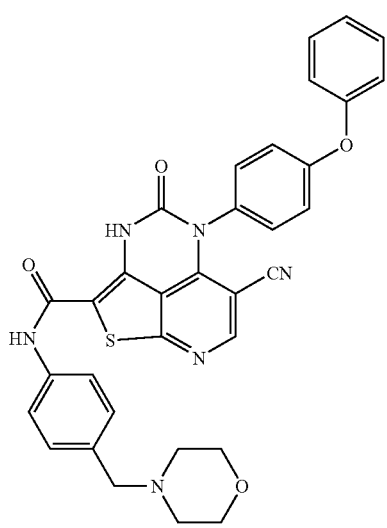

Cpd 51
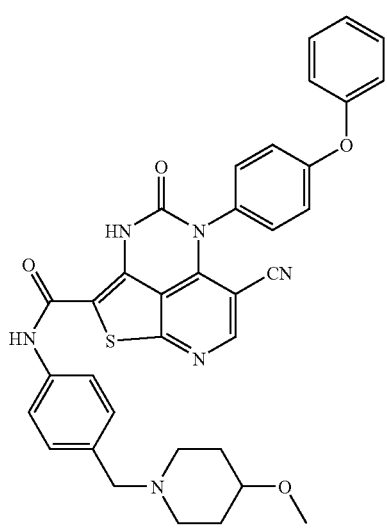

-continued

Cpd 52
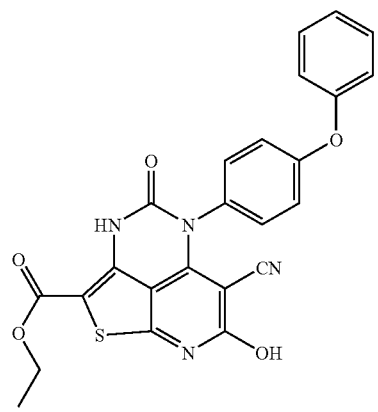

Cpd 53

Cpd 54

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$alkyl" means a saturated aliphatic branched or straight-chain hydrocarbon radical or linking group having from 1 up to 8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" also includes a "$C_{1-6}$alkyl" and "$C_{1-4}$alkyl" radical or linking group having from 1 up to 6 carbon atoms and 1 up to 4 carbon atoms respectively, such as methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Alkyl radicals may be attached to a core molecule and further substituted on any atom when allowed by available valences.

The term "$C_{1-8}$alkoxy" means an alkyl radical or linking group having from 1 up to 8 carbon atoms in a linear or branched arrangement, wherein the radical or linking group is attached through an oxygen linking atom, as in the formula: —O—$C_{1-8}$alkyl. The term "$C_{1-8}$alkoxy" also includes a "$C_{1-6}$alkoxy" and "$C_{1-4}$alkoxy" radical or linking group having from 1 up to 6 carbon atoms and from 1 up to 4 carbon atoms respectively, such as methoxy, ethoxy, propoxy, butoxy and the like. An alkoxy radical may be attached to a core molecule and further substituted on any atom when allowed by available valences.

The term "$C_{3-12}$cycloalkyl" means a saturated or partially unsaturated cyclic hydrocarbon ring system radical. The term "$C_{3-12}$cycloalkyl" also includes a $C_{3-8}$cycloalkyl, $C_{3-10}$-cycloalkyl, $C_{5-6}$cycloalkyl, $C_{5-8}$cycloalkyl, $C_{5-12}$cycloalkyl, $C_{9-13}$cycloalkyl or benzofused-$C_{3-12}$cycloalkyl ring system radical and the like, such as cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, acenaphthenyl, adamantanyl and the like. $C_{3-12}$cycloalkyl radicals may be attached to a core molecule and further substituted on any atom when allowed by available valences.

The term "aryl" means an unsaturated aromatic hydrocarbon ring system radical. Aryl ring systems include phenyl, naphthalenyl, azulenyl, anthracenyl and the like. Examples of aryl in compounds representative of the present invention include phenyl or naphthalenyl. Aryl radicals may be attached to a core molecule and further substituted on any atom when allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated "hetero" ring system radical. Heterocyclyl ring systems include azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azepanyl, hexahydro-1,4-diazepinyl, hexahydro-1,4-oxazepanyl, tetrahydro-furanyl, tetrahydrothienyl, tetrahydro-pyranyl, tetrahydro-pyridazinyl and the like. Heterocyclyl radicals may be attached to a core molecule and further substituted on any atom when allowed by available valences.

The term "benzofused heterocyclyl" also includes a heterocyclyl ring system radical and the like, such as indolinyl (also referred to as 2,3-dihydro-indolyl), benzo[1,3]dioxolyl, 2,3-dihydro-1,4-benzodioxinyl, 2,3-dihydro-benzofuranyl, 1,2-dihydro-phthalazinyl and the like. Benzofused heterocyclyl radicals may be attached to a core molecule and further substituted on any atom when allowed by available valences.

The term "heteroaryl" means an unsaturated aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like. Heteroaryl radicals may be attached to a core molecule and further substituted on any atom when allowed by available valences.

The term "benzofused heteroaryl" also includes a heteroaryl ring system radical and the like, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. Benzofused-heteroaryl radicals may be attached to a core molecule and further substituted on any atom when allowed by available valences.

The term "$C_{1-8}$alkoxy-($C_{1-8}$)alkyl" means a radical of the formula: —$C_{1-8}$alkyl-O—$C_{1-8}$alkyl.

The term "$C_{1-8}$alkoxy-carbonyl" means a radical of the formula: —C(O)—O—$C_{1-8}$alkyl.

The term "$C_{1-8}$alkoxy-carbonyl-amino" means a radical of the formula: —NH—C(O)—O—$C_{1-8}$alkyl or —N[C(O)—O—$C_{1-8}$alkyl]$_2$.

The term "$C_{1-8}$alkyl-amino" means a radical of the formula: —NH—$C_{1-8}$alkyl or —N($C_{1-8}$alkyl)$_2$.

The term "$C_{1-8}$alkyl-amino-($C_{1-8}$)alkyl" means a radical of the formula: —$C_{1-8}$alkyl-NH—$C_{1-8}$alkyl, —$C_{1-8}$alkyl-N($C_{1-8}$ alkyl)$_2$, —$C_{1-8}$alkyl-NH—($C_{1-8}$alkyl-terminal group), —$C_{1-8}$alkyl-N($C_{1-8}$alkyl-terminal group)$_2$ or —$C_{1-8}$alkyl-N($C_{1-8}$alkyl)-$C_{1-8}$alkyl-terminal group.

The term "amino" means a radical of the formula: —$NH_2$.

The term "amino-($C_{1-8}$)alkyl" means a radical of the formula: —$C_{1-8}$alkyl-$NH_2$.

The term "aryl-oxy" means a radical of the formula: —O-aryl.

The term "$C_{3-8}$cycloalkyl-amino" means a radical of the formula: —NH—$C_{3-8}$cycloalkyl or —N($C_{3-8}$cycloalkyl)$_2$.

The term "halogen" or "halo" means the group chloro, bromo, fluoro or iodo.

The term "halo-($C_{1-8}$)alkoxy" means a radical of the formula: —O—$C_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethoxy, difluoromethoxy, trifluoromethoxy, trifluoroethoxy and the like.

The term "halo-($C_{1-8}$)alkyl" means a radical of the formula: —$C_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethyl, difluoromethyl, trifluoromethyl, trifluoroethyl and the like.

The term "heteroaryl-oxy" means a radical of the formula: —O-heteroaryl.

The term "heterocyclyl-amino" means a radical of the formula: —NH-heterocyclyl or —N(heterocyclyl)$_2$.

The term "heterocyclyl-($C_{1-8}$)alkyl-amino" means a radical of the formula: —NH—$C_{1-8}$alkyl-heterocyclyl or —N($C_{1-8}$alkyl-heterocyclyl)$_2$.

The term "hydroxy-($C_{1-8}$)alkoxy" means a radical of the formula: —O—$C_{1-8}$alkyl-hydroxy, wherein $C_{1-8}$alkyl is substituted on one or more available carbon chain atoms with one or more hydroxy radicals when allowed by available valences.

The term "hydroxy-($C_{1-8}$)alkyl" means a radical of the formula: —$C_{1-8}$alkyl-hydroxy, wherein $C_{1-8}$alkyl is substituted on one or more available carbon chain atoms with one or more hydroxy radicals when allowed by available valences.

The term "substituted" means the independent replacement of one or more hydrogen atoms within a radical with that amount of substitutents allowed by available valences.

The term "dependently selected" means that the structure variables are specified in an indicated combination.

The term "terminal group" means a moiety attached on a radical substituent chain that serves as the last group of atoms on the chain.

In general, IUPAC nomenclature rules are used herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof. In an embodiment the term "form" means salts, in particular pharmaceutically acceptable salts, stereoisomers, and solvates of the compounds.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, glycoate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

Examples of salt forms of compounds representative of the present invention include the monohydrochloride salt.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each isolated specie rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have at least one crystalline, polymorph or amorphous form. The plurality of such forms are intended to be included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

Methods of Use

The compounds of formula (I) are inhibitors of a protein kinase such as EGFR, HER-2, c-Src, Lyn, c-Abl, Aurora-A or VEGF, having an $IC_{50}$ (50% inhibition concentration) or an $EC_{50}$ (50% effective concentration) in a range of about 50 µM or less, of about 25 µM or less, of about 15 µM or less, of about 10 µM or less, of about 5 µM or less, of about 1 µM or less, of about 0.5 µM or less, of about 0.25 µM or less or of about 0.1 µM or less.

The present invention includes a compound of formula (I) and forms thereof as a protein kinase inhibitor, wherein the protein kinase is selected from EGFR, HER-2, c-Src, Lyn, c-Abl, Aurora-A or VEGF.

The present invention includes a prodrug form of a compound of formula (I) and forms thereof as a protein kinase inhibitor.

The present invention includes a metabolite form of a compound of formula (I) and forms thereof as a protein kinase inhibitor.

The present invention includes an isolated form of a compound of formula (I) and forms thereof as a protein kinase inhibitor.

The present invention includes a compound of formula (I) or a form thereof, wherein the compound is labeled with a ligand for use as a marker, and wherein the ligand is a radioligand selected from deuterium, tritium and the like.

The present invention includes use of a compound of formula (I) and forms thereof as an inhibitor of a protein kinase such as EGFR, HER-2, c-Src, Lyn, c-Abl, Aurora-A or VEGF comprising contacting the protein kinase domain or receptor with the compound.

The present invention includes the use of a compound of formula (I) and forms thereof as a pharmaceutical composition, medicine or medicament for treating, preventing or ameliorating a kinase mediated disease, disorder or condition.

The present invention includes the use of a compound of formula (I) and forms thereof as a medicament.

The present invention includes the use of a compound of formula (I) and forms thereof in the manufacture of a medicament for treating, preventing or ameliorating a kinase mediated disease, disorder or condition.

The present invention includes the use of a prodrug of a compound of formula (I) and forms thereof as a pharmaceutical composition, medicine or medicament for treating, preventing or ameliorating a kinase mediated disease, disorder or condition.

The present invention includes the use of a prodrug of a compound of formula (I) and forms thereof as a medicament.

The present invention is directed to a method for treating, preventing or ameliorating a chronic or acute protein kinase mediated disease, disorder or condition in a subject in need thereof comprising administering to the subject an effective amount of a compound of formula (I) and forms thereof.

The method of the present invention further comprises administering to the subject an effective amount of a prodrug of a compound of formula (I) and forms thereof.

The method of the present invention further comprises treating, preventing or ameliorating a chronic or acute EGFR, HER-2, c-Src, Lyn, c-Abl, Aurora-A or VEGF mediated disease, disorder or condition.

The method of the present invention wherein the disease, disorder or condition is associated with increased or unregulated protein kinase activity, expression or signaling and the like in the subject.

The method of the present invention further comprises administering to the subject an effective amount of a compound of formula (I) as a pharmaceutical composition, medicine or medicament thereof.

The method of the present invention wherein the disease, disorder or condition is an EGFR kinase mediated head or brain cancer in the subject, and wherein the compound penetrates the blood brain barrier.

The method of the present invention further comprises treating or ameliorating nerve damage and promoting axon regeneration subsequent to a brain or spinal cord injury in the subject, wherein the compound is an EGFR inhibitor.

The method of the present invention further comprises treating, preventing or ameliorating viral infection by an EGFR kinase mediated cytomegalovirus in the subject.

The term "chronic or acute protein kinase mediated disease, disorder or condition" as used herein, includes, and is not limited to diseases, disorders or conditions associated with unregulated kinase activity and conditions that accompany such activity.

The term "unregulated protein kinase activity, expression or signaling" refers to 1) increased or unregulated kinase expression or signaling, 2) increased kinase expression leading to unregulated cell proliferation, 3) increased kinase signalling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that a compound of formula (I) or a form thereof is useful for treating, preventing or ameliorating diseases, disorders or conditions such as, without limitation, osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohns disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, occular diseases, viral infections, heart disease, lung or pulmonary diseases or kidney or renal diseases.

Certain diseases, disorders or conditions further include, without limitation, acute or chronic cancer selected from bladder cancer, brain, head or neck cancer, breast cancer, colorectal cancer, endometrial cancer, epidermoid cancer, esophageal cancer, gastric cancer, glioma cancer, lung cancer, ovarian cancer, pancreatic cancer, prostate cancer, renal cell cancer, Kaposi's sarcoma, leukemia, lymphoma or papillocarcinoma; and, cancer-associated pathologies selected from abnormal cell proliferation, unregulated cell proliferation, tumor growth, tumor angiopathy, tumor angiogenesis, tumor vascularization or metastatic cancer cell invasion and migration.

Certain diseases, disorders or conditions further include, without limitation, fibroproliferative and differentiative skin diseases or disorders selected from papilloma formation, psoriasis, dermatitis, eczema, seborrhea or chemotherapy-induced alopecia; central nervous system diseases selected from Alzheimer's disease, Parkinson's disease or depression; occular diseases selected from macular degeneration, diseases of the cornea or glaucoma; viral infections selected from mycotic infection, autoimmune disease or cytomegalovirus; heart disease selected from atherosclerosis, neointima formation or transplantation-induced vasculopathies such as arterial restenosis; lung or pulmonary diseases selected from allergic-asthma, lung fibrosis, pulmonary fibrosis or chronic obstructive pulmonary disorder; and, kidney or renal diseases selected from acute, subacute or chronic forms of glomerulonephritis or membranoproliferative glomerulonephritis, glomerulosclerosis, congenital multicystic renal dysplasia or kidney fibrosis.

Certain HER1 kinase mediated cancer includes, without limitation, bladder cancer, brain, head or neck cancer, breast cancer, cervical cancer, colorectal cancer, gastric cancer, glioma cancer, endometrial cancer, esophageal cancer, lung cancer, ovarian cancer, pancreatic cancer or renal cell cancer.

Certain HER2 kinase mediated cancer includes, without limitation, bladder cancer, brain, head or neck cancer, breast cancer, colorectal cancer, gastric cancer, endometrial cancer, esophageal cancer, lung cancer, ovarian cancer, prostate cancer or renal cell cancer.

The term "administering," with respect to the methods of the present invention, refers to a means for treating, ameliorating or preventing a disease, disorder or syndrome as described herein with a compound of formula (I) or a form thereof, which would obviously be included within the scope of the invention albeit not specifically disclosed for certain of said compounds.

Such methods include therapeutically or prophylactically administering an effective amount of compound of formula (I) or a form thereof at different times during the course of a therapy or concurrently in a combination form. Such methods further include administering an effective amount of said compound with one or more agents at different times during the course of a therapy or concurrently in a combination form.

The term "prodrug" means a compound of formula (I) or a form thereof that is converted in vivo into a functional derivative form that may contribute to therapeutic biological activity, wherein the converted form may be: 1) a relatively active form; 2) a relatively inactive form; 3) a relatively less active form; or, 4) any form which results, directly or indirectly, from such in vivo conversions.

Prodrugs are useful when said compound may be either too toxic to administer systemically, absorbed poorly by the digestive tract or broken down by the body before it reaches its target. Conventional procedures for the selection and preparation of suitable prodrug derivatives are described in, for example, "*Design of Prodrugs*", ed. H. Bundgaard, Elsevier, 1985.

The term "metabolite" means a prodrug form of a compound of formula (I) or a form thereof converted by in vivo metabolism or a metabolic process to a relatively less active functional derivative of said compound.

The term "subject" as used herein, refers to a patient, such as an animal, a mammal or a human, who has been the object of treatment, observation or experiment and is at risk of (or susceptible to) developing a disease or disorder or having a disease or disorder related to unregulated kinase activity.

The term "effective amount" refers to that amount of a compound of formula (I) or a form, pharmaceutical composition, medicine or medicament thereof that elicits the biological or medicinal response (such as inhibiting activation of unregulated kinase activity) in a tissue system, animal or human, that is being sought by a researcher, veterinarian, medical doctor, or other clinician, which includes alleviation of the symptoms of the disease or disorder being treated. The effective amount of a certain compound can be assessed by the skilled person in a art-known manner.

The effective amount of said compound is from about 0.001 mg/kg/day to about 300 mg/kg/day.

The term "pharmaceutical composition" refers to a product containing a compound of formula (I) or a form thereof, such as a product comprising the specified ingredients in the specified amounts, as well as any product which results, directly or indirectly, from such combinations of the specified ingredients in the specified amounts.

The term "medicament" or "medicine" refers to a product containing a compound of formula (I) or a form thereof. The present invention includes use of such a medicament for treating, preventing or ameliorating a chronic or acute kinase mediated disease, disorder or condition.

The term "pharmaceutically acceptable" refers to molecular entities and compositions that are of sufficient purity and quality for use in the formulation of a pharmaceutical composition, medicine or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a pharmaceutical composition, medicine or medicament for either human or veterinary use.

The term "combination form" refers to the use of a combination product comprising a compound of formula (I) or a form, pharmaceutical composition, medicine or medicament thereof and at least one therapeutic agent for treating, preventing or ameliorating a chronic or acute protein kinase mediated disease, disorder or condition.

Advantageously, the effective amount of a combination product for treating, preventing or ameliorating a chronic or acute protein kinase mediated disease, disorder or condition may be a reduced amount of either or both the compound or therapeutic agent compared to the effective amount of the compound or therapeutic agent otherwise recommended for treating, preventing or ameliorating the disease, disorder or condition. Therefore, it is contemplated that the compound is administered to the subject before, during or after the time the agent is administered.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or a combination thereof.

The term "treating, preventing or ameliorating" refers, without limitation, to facilitating the eradication of, inhibiting the progression of or promoting stasis of a chronic or acute kinase mediated disease, disorder or condition.

The term "radiation therapy" refers to a therapy that comprises exposing the subject in need thereof to radiation. The present invention includes a method for administering a compound of formula (I) or a form, pharmaceutical composition, medicine or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

The present invention includes a pharmaceutical composition comprising an admixture of a compound of formula (I) or a form thereof and one or more pharmaceutically acceptable excipients.

The present invention includes a process for making a pharmaceutical composition, medicine or medicament comprising mixing a compound of formula (I) or a form thereof and an optional pharmaceutically acceptable carrier. The present invention includes a pharmaceutical composition, medicine or medicament resulting from the process of mixing a compound of formula (I) or a form thereof and an optional pharmaceutically acceptable carrier. Contemplated processes include both conventional and unconventional pharmaceutical techniques.

Said pharmaceutical composition, medicine or medicament may take a wide variety of forms to effectuate mode of administration, wherein the mode includes, and is not limited to, intravenous (both bolus and infusion), oral, nasal, transdermal, topical with or without occlusion, and via injection intraperitoneally, subcutaneously, intramuscularly, intratumorally, intracerebrally or intracranially. The composition, medicine or medicament may be in a dosage unit such as a tablet, pill, capsule, powder, granule, sterile parenteral solution or suspension, metered aerosol or liquid spray, drop, ampoule, auto-injector device or suppository for such administration modes.

Pharmaceutical compositions, medicines or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the pharmaceutical composition, medicine or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the pharmaceutical composition, medicine or medicament contains an effective amount of the active ingredient necessary to be therapeutically or prophylactically effective as described above. The pharmaceutical composition, medicine or medicament may contain from about 0.001 mg to about 5000 mg (preferably, from about 0.001 to about 500 mg) of a compound of formula (I) or a form thereof and may be constituted into any form suitable for the mode of administration selected for a subject in need.

An example of a contemplated effective amount for a pharmaceutical composition, medicine or medicament of the present invention may range from about 0.001 mg to about 300 mg/kg of body weight per day. In another example, the range is from about 0.003 to about 100 mg/kg of body weight per day. In another example, the range is from about 0.005 to about 15 mg/kg of body weight per day. The pharmaceutical composition, medicine or medicament may be administered according to a dosage regimen of from about 1 to about 5 times per day.

For oral administration, the pharmaceutical composition, medicine or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of a compound of formula (I) or a form thereof for the symptomatic adjustment of the dosage to the patient to be treated. Optimal dosages will vary depending on factors associated with the particular patient being treated (e.g., age, weight, diet and time of administration), the severity of the condition being treated, the particular compound being used, the mode of administration and the strength of the preparation. The use of either daily administration or post-periodic dosing may be employed.

A representative compound of formula (I) or a form thereof includes a compound selected from:

| Cpd | Name |
|---|---|
| 1 | 5-(2-chloro-phenyl)-6-cyano-7-hydroxy-4-oxo-4,5-dihydro-3H-1-thia-3,5,8-triaza-acenaphthylene-2-carboxylic acid ethyl ester, |
| 2 | 5-(2-chloro-phenyl)-6-cyano-4-oxo-4,5-dihydro-3H-1-thia-3,5,8-triaza-acenaphthylene-2-carboxylic acid (4-piperidin-1-ylmethyl-phenyl)-amide, |
| 3 | 5-(2-chloro-phenyl)-6-cyano-4-oxo-4,5-dihydro-3H-1-thia-3,5,8-triaza-acenaphthylene-2-carboxylic acid (4-morpholin-4-ylmethyl-phenyl)-amide, |
| 4 | 5-(5-chloro-benzo[1,3]dioxol-4-yl)-6-cyano-4-oxo-4,5-dihydro-3H-1-thia-3,5,8-triaza-acenaphthylene-2-carboxylic acid (4-morpholin-4-ylmethyl-phenyl)-amide, |
| 5 | 6-cyano-5-(2,4-dichloro-5-methoxy-phenyl)-4-oxo-4,5-dihydro-3H-1-thia-3,5,8-triaza-acenaphthylene-2-carboxylic acid (4-morpholin-4-ylmethyl-phenyl)-amide, |
| 6 | 6-cyano-5-(2,4-dichloro-5-methoxy-phenyl)-4-oxo-4,5-dihydro-3H-1-thia-3,5,8-triaza-acenaphthylene-2-carboxylic acid [4-(2-morpholin-4-yl-ethyl)-phenyl]-amide, |
| 7 | 5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid ethyl ester, |
| 8 | 5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid (4-morpholin-4-ylmethyl-phenyl)-amide, |
| 9 | 5-(5-chloro-benzo[1,3]dioxol-4-yl)-6-cyano-7-methyl-4-oxo-4,5-dihydro-3H-1-thia-3,5,8-triaza-acenaphtylene-2-carboxylic acid (4-morpholin-4-ylmethyl-phenyl)-amide, |
| 10 | 5-(5-chloro-benzo[1,3]dioxol-4-yl)-6-cyano-4-oxo-4,5-dihydro-3H-1-thia-3,5,8-triaza-acenaphthylene-2-carboxylic acid (1-methyl-piperidin-4-yl)-amide, |
| 11 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2-piperidin-1-yl-ethyl)-phenyl]-amide, |
| 12 | 5-(5-chloro-benzo[1,3]dioxol-4-yl)-6-cyano-4-oxo-4,5-dihydro-3H-1-thia-3,5,8-triaza-acenaphthylene-2-carboxylic acid {4-[2-(4-methyl-piperazin-1-yl)-ethyl]-phenyl}-amide, |
| 13 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2-morpholin-4-yl-ethyl)-phenyl]-amide, |
| 14 | 6-cyano-7-hydroxy-4-oxo-5-pyridin-4-yl-4,5-dihydro-3H-1-thia-3,5,8-triaza-acenaphthylene-2-carboxylic acid ethyl ester, |
| 15 | 7-(2-chloro-5-fluoro-phenyl)-6-cyano-4-oxo-5-pyridin-4-yl-4,5-dihydro-3H-1-thia-3,5,8-triaza-acenaphthylene-2-carboxylic acid ethyl ester, |
| 16 | 7-(2-chloro-5-fluoro-phenyl)-6-cyano-4-oxo-5-pyridin-4-yl-4,5-dihydro-3H-1-thia-3,5,8-triaza-acenaphthylene-2-carboxylic acid (2-pyrrolidin-1-yl-ethyl)-amide, |
| 17 | 5-(5-chloro-benzo[1,3]dioxol-4-yl)-6-cyano-4-oxo-4,5-dihydro-3H-1-thia-3,5,8-triaza-acenaphthylene-2-carboxylic acid ethyl ester, |
| 18 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methoxy-piperidin-1-ylmethyl)-phenyl]-amide, |
| 19 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methyl-piperidin-1-ylmethyl)-phenyl]-amide, |
| 20 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3-hydroxymethyl-piperidin-1-ylmethyl)-phenyl]-amide, |
| 21 | 5-(5-chloro-benzo[1,3]dioxol-4-yl)-2-(3-hydroxymethyl-piperidine-1-carbonyl)-4-oxo-4,5-dihydro-3H-1-thia-3,5,8-triaza-acenaphthylene-6-carbonitrile, |
| 22 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxymethyl-piperidin-1-ylmethyl)-phenyl]-amide, |
| 23 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxy-piperidin-1-ylmethyl)-phenyl]-amide, |
| 24 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3,5-dimethyl-morpholin-4-ylmethyl)-phenyl]-amide, |
| 25 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2,6-cis-dimethyl-morpholin-4-ylmethyl)-phenyl]-amide, |
| 26 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-fluoro-piperidin-1-ylmethyl)-phenyl]-amide, |
| 27 | 5-(5-chloro-benzo[1,3]dioxol-4-yl)-6-cyano-4-oxo-4,5-dihydro-3H-1-thia-3,5,8-triaza-acenaphthylene-2-carboxylic acid (3-dimethylamino-4-morpholin-4-ylmethyl-phenyl)-amide, |
| 28 | 5-(5-chloro-benzo[1,3]dioxol-4-yl)-2-(4-hydroxy-piperidine-1-carbonyl)-4-oxo-4,5-dihydro-3H-1-thia-3,5,8-triaza-acenaphthylene-6-carbonitrile, |

-continued

| Cpd | Name |
|---|---|
| 29 | 5-(5-chloro-benzo[1,3]dioxol-4-yl)-6-cyano-4-oxo-4,5-dihydro-3H-1-thia-3,5,8-triaza-acenaphthylene-2-carboxylic acid methyl-(4-morpholin-4-ylmethyl-phenyl)-amide, |
| 30 | 5-(5-chloro-benzo[1,3]dioxol-4-yl)-6-cyano-4-oxo-4,5-dihydro-3H-1-thia-3,5,8-triaza-acenaphthylene-2-carboxylic acid [6-(3-morpholin-4-yl-propylamino)-pyridin-3-yl]-amide, |
| 31 | 5-(5-chloro-benzo[1,3]dioxol-4-yl)-6-cyano-4-oxo-4,5-dihydro-3H-1-thia-3,5,8-triaza-acenaphthylene-2-carboxylic acid [3-methoxy-4-(2-piperidin-1-yl-ethoxy)-phenyl]-amide, |
| 32 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(1-methyl-piperidin-2-ylmethoxy)-phenyl]-amide, |
| 33 | 5-(5-chloro-benzo[1,3]dioxol-4-yl)-6-cyano-4-oxo-4,5-dihydro-3H-1-thia-3,5,8-triaza-acenaphthylene-2-carboxylic acid (1H-pyrazol-3-yl)-amide, |
| 34 | 5-(5-chloro-benzo[1,3]dioxol-4-yl)-6-cyano-4-oxo-4,5-dihydro-3H-1-thia-3,5,8-triaza-acenaphthylene-2-carboxylic acid (5-methyl-isoxazol-3-yl)-amide, |
| 35 | 5-(5-chloro-benzo[1,3]dioxol-4-yl)-6-cyano-4-oxo-4,5-dihydro-3H-1-thia-3,5,8-triaza-acenaphthylene-2-carboxylic acid pyrimidin-2-ylamide, |
| 36 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-3-ylamide, |
| 37 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-2-ylamide, |
| 38 | 5-(5-chloro-benzo[1,3]dioxol-4-yl)-6-cyano-4-oxo-4,5-dihydro-3H-1-thia-3,5,8-triaza-acenaphthylene-2-carboxylic acid (2-hydroxy-1,1-dimethyl-ethyl)-amide, |
| 39 | 5-(5-chloro-benzo[1,3]dioxol-4-yl)-6-cyano-4-oxo-4,5-dihydro-3H-1-thia-3,5,8-triaza-acenaphthylene-2-carboxylic acid (1-methyl-1H-pyrazol-3-yl)-amide, |
| 40 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-4-ylamide, |
| 41 | 5-(5-chloro-benzo[1,3]dioxol-4-yl)-2-(4-dimethylamino-piperidine-1-carbonyl)-4-oxo-4,5-dihydro-3H-1-thia-3,5,8-triaza-acenaphthylene-6-carbonitrile, |
| 42 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-dimethylamino-piperidin-1-ylmethyl)-phenyl]-amide, |
| 43 | 5-(5-chloro-benzo[1,3]dioxol-4-yl)-2-(3-fluoro-piperidine-1-carbonyl)-4-oxo-4,5-dihydro-3H-1-thia-3,5,8-triaza-acenaphthylene-6-carbonitrile, |
| 44 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3-fluoro-piperidin-1-ylmethyl)-phenyl]-amide, |
| 45 | 6-cyano-4-oxo-5-(4-phenoxy-phenyl)-4,5-dihydro-3H-1-thia-3,5,8-triaza-acenaphthylene-2-carboxylic acid (3-methoxy-4-morpholin-4-ylmethyl-phenyl)-amide, |
| 46 | [1-(4-{[5-(5-chloro-benzo[1,3]dioxol-4-yl)-6-cyano-4-oxo-4,5-dihydro-3H-1-thia-3,5,8-triaza-acenaphthylene-2-carbonyl]-amino}-benzyl)-piperidin-4-yl]-carbamic acid tert-butyl ester, |
| 47 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-amino-piperidin-1-ylmethyl)-phenyl]-amide, |
| 48 | 6-cyano-4-oxo-5-(4-phenoxy-phenyl)-4,5-dihydro-3H-1-thia-3,5,8-triaza-acenaphthylene-2-carboxylic acid [4-(2-piperidin-1-yl-ethyl)-phenyl]-amide, |
| 49 | 6-cyano-4-oxo-5-(4-phenoxy-phenyl)-4,5-dihydro-3H-1-thia-3,5,8-triaza-acenaphthylene-2-carboxylic acid (4-piperidin-1-ylmethyl-phenyl)-amide, |
| 50 | 6-cyano-4-oxo-5-(4-phenoxy-phenyl)-4,5-dihydro-3H-1-thia-3,5,8-triaza-acenaphthylene-2-carboxylic acid (4-morpholin-4-ylmethyl-phenyl)-amide, |
| 51 | 6-cyano-4-oxo-5-(4-phenoxy-phenyl)-4,5-dihydro-3H-1-thia-3,5,8-triaza-acenaphthylene-2-carboxylic acid [4-(4-methoxy-piperidin-1-ylmethyl)-phenyl]-amide, |
| 52 | 6-cyano-7-hydroxy-4-oxo-5-(4-phenoxy-phenyl)-4,5-dihydro-3H-1-thia-3,5,8-triaza-acenaphthylene-2-carboxylic acid ethyl ester, |
| 53 | 7-chloro-6-cyano-4-oxo-5-(4-phenoxy-phenyl)-4,5-dihydro-3H-1-thia-3,5,8-triaza-acenaphthylene-2-carboxylic acid ethyl ester, or |
| 54 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4,4-difluoro-piperidin-1-ylmethyl)-phenyl]-amide. |

A representative compound of formula (I) or a form thereof includes a compound selected from:

| Cpd | Name |
|---|---|
| 3 | 5-(2-chloro-phenyl)-6-cyano-4-oxo-4,5-dihydro-3H-1-thia-3,5,8-triaza-acenaphthylene-2-carboxylic acid (4-morpholin-4-ylmethyl-phenyl)-amide, |
| 4 | 5-(5-chloro-benzo[1,3]dioxol-4-yl)-6-cyano-4-oxo-4,5-dihydro-3H-1-thia-3,5,8-triaza-acenaphthylene-2-carboxylic acid (4-morpholin-4-ylmethyl-phenyl)-amide, |
| 5 | 6-cyano-5-(2,4-dichloro-5-methoxy-phenyl)-4-oxo-4,5-dihydro-3H-1-thia-3,5,8-triaza-acenaphthylene-2-carboxylic acid (4-morpholin-4-ylmethyl-phenyl)-amide, |
| 6 | 6-cyano-5-(2,4-dichloro-5-methoxy-phenyl)-4-oxo-4,5-dihydro-3H-1-thia-3,5,8-triaza-acenaphthylene-2-carboxylic acid [4-(2-morpholin-4-yl-ethyl)-phenyl]-amide, |
| 7 | 5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid ethyl ester, |
| 8 | 5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid (4-morpholin-4-ylmethyl-phenyl)-amide, |
| 9 | 5-(5-chloro-benzo[1,3]dioxol-4-yl)-6-cyano-7-methyl-4-oxo-4,5-dihydro-3H-1-thia-3,5,8-triaza-acenaphthylene-2-carboxylic acid (4-morpholin-4-ylmethyl-phenyl)-amide, |
| 10 | 5-(5-chloro-benzo[1,3]dioxol-4-yl)-6-cyano-4-oxo-4,5-dihydro-3H-1-thia-3,5,8-triaza-acenaphthylene-2-carboxylic acid (1-methyl-piperidin-4-yl)-amide, |
| 11 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2-piperidin-1-yl-ethyl)-phenyl]-amide, |
| 12 | 5-(5-chloro-benzo[1,3]dioxol-4-yl)-6-cyano-4-oxo-4,5-dihydro-3H-1-thia-3,5,8-triaza-acenaphthylene-2-carboxylic acid {4-[2-(4-methyl-piperazin-1-yl)-ethyl]-phenyl}-amide, |
| 18 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methoxy-piperidin-1-ylmethyl)-phenyl]-amide, |
| 19 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methyl-piperidin-1-ylmethyl)-phenyl]-amide, |
| 20 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3-hydroxymethyl-piperidin-1-ylmethyl)-phenyl]-amide, |
| 21 | 5-(5-chloro-benzo[1,3]dioxol-4-yl)-2-(3-hydroxymethyl-piperidine-1-carbonyl)-4-oxo-4,5-dihydro-3H-1-thia-3,5,8-triaza-acenaphthylene-6-carbonitrile, |
| 22 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxymethyl-piperidin-1-ylmethyl)-phenyl]-amide, |
| 23 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxy-piperidin-1-ylmethyl)-phenyl]-amide, |
| 27 | 5-(5-chloro-benzo[1,3]dioxol-4-yl)-6-cyano-4-oxo-4,5-dihydro-3H-1-thia-3,5,8-triaza-acenaphthylene-2-carboxylic acid (3-dimethylamino-4-morpholin-4-ylmethyl-phenyl)-amide, |
| 28 | 5-(5-chloro-benzo[1,3]dioxol-4-yl)-2-(4-hydroxy-piperidine-1-carbonyl)-4-oxo-4,5-dihydro-3H-1-thia-3,5,8-triaza-acenaphthylene-6-carbonitrile, |
| 30 | 5-(5-chloro-benzo[1,3]dioxol-4-yl)-6-cyano-4-oxo-4,5-dihydro-3H-1-thia-3,5,8-triaza-acenaphthylene-2-carboxylic acid [6-(3-morpholin-4-yl-propylamino)-pyridin-3-yl]-amide, |
| 31 | 5-(5-chloro-benzo[1,3]dioxol-4-yl)-6-cyano-4-oxo-4,5-dihydro-3H-1-thia-3,5,8-triaza-acenaphthylene-2-carboxylic acid [3-methoxy-4-(2-piperidin-1-yl-ethoxy)-phenyl]-amide, |
| 32 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(1-methyl-piperidin-2-ylmethoxy)-phenyl]-amide, |
| 33 | 5-(5-chloro-benzo[1,3]dioxol-4-yl)-6-cyano-4-oxo-4,5-dihydro-3H-1-thia-3,5,8-triaza-acenaphthylene-2-carboxylic acid (1H-pyrazol-3-yl)-amide, |
| 34 | 5-(5-chloro-benzo[1,3]dioxol-4-yl)-6-cyano-4-oxo-4,5-dihydro-3H-1-thia-3,5,8-triaza-acenaphthylene-2-carboxylic acid (5-methyl-isoxazol-3-yl)-amide, |
| 35 | 5-(5-chloro-benzo[1,3]dioxol-4-yl)-6-cyano-4-oxo-4,5-dihydro-3H-1-thia-3,5,8-triaza-acenaphthylene-2-carboxylic acid pyrimidin-2-ylamide, |
| 36 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-3-ylamide, |
| 40 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-4-ylamide, |
| 42 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-dimethylamino-piperidin-1-ylmethyl)-phenyl]-amide, |

| Cpd | Name |
|---|---|
| 45 | 6-cyano-4-oxo-5-(4-phenoxy-phenyl)-4,5-dihydro-3H-1-thia-3,5,8-triaza-acenaphthylene-2-carboxylic acid (3-methoxy-4-morpholin-4-ylmethyl-phenyl)-amide, |
| 46 | [1-(4-{[5-(5-chloro-benzo[1,3]dioxol-4-yl)-6-cyano-4-oxo-4,5-dihydro-3H-1-thia-3,5,8-triaza-acenaphthylene-2-carbonyl]-amino}-benzyl)-piperidin-4-yl]-carbamic acid tert-butyl ester, |
| 47 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-amino-piperidin-1-ylmethyl)-phenyl]-amide, |
| 48 | 6-cyano-4-oxo-5-(4-phenoxy-phenyl)-4,5-dihydro-3H-1-thia-3,5,8-triaza-acenaphthylene-2-carboxylic acid [4-(2-piperidin-1-yl-ethyl)-phenyl]-amide, |
| 49 | 6-cyano-4-oxo-5-(4-phenoxy-phenyl)-4,5-dihydro-3H-1-thia-3,5,8-triaza-acenaphthylene-2-carboxylic acid (4-piperidin-1-ylmethyl-phenyl)-amide, |
| 50 | 6-cyano-4-oxo-5-(4-phenoxy-phenyl)-4,5-dihydro-3H-1-thia-3,5,8-triaza-acenaphthylene-2-carboxylic acid (4-morpholin-4-ylmethyl-phenyl)-amide, |
| 51 | 6-cyano-4-oxo-5-(4-phenoxy-phenyl)-4,5-dihydro-3H-1-thia-3,5,8-triaza-acenaphthylene-2-carboxylic acid [4-(4-methoxy-piperidin-1-ylmethyl)-phenyl]-amide, or |
| 52 | 6-cyano-7-hydroxy-4-oxo-5-(4-phenoxy-phenyl)-4,5-dihydro-3H-1-thia-3,5,8-triaza-acenaphthylene-2-carboxylic acid ethyl ester. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations or formulas have the indicated meanings:

| Abbreviation | Meaning |
|---|---|
| $CH_3CN$ | acetonitrile |
| CDI | carbodiimide |
| Cpd | compound |
| DIPEA | diisopropylethylamine |
| DMF | N,N-dimethyl formamide |
| DMSO | dimethyl sulfoxide |
| DME | ethylene glycol dimethyl ether |
| DCM | dichloromethane |
| EtOAc | ethyl acetate |
| HATU | O-(7-azabenzotriazol-1-yl)-N,N,N',N'-tetramethyluronium hexafluorophosphate |
| KOtBu | potassium t-butoxide |
| min(s)/hr(s) | minute(s)/hour(s) |
| PyBOP | (benzotriazol-1-yloxy)tripyrrolidinophosphonium hexafluorophosphate |
| RT/rt/r.t. | room temperature |
| TEA or $Et_3N$ | triethylamine |
| TFA | trifluoroacetic acid |
| THF | tetrahydrofuran |

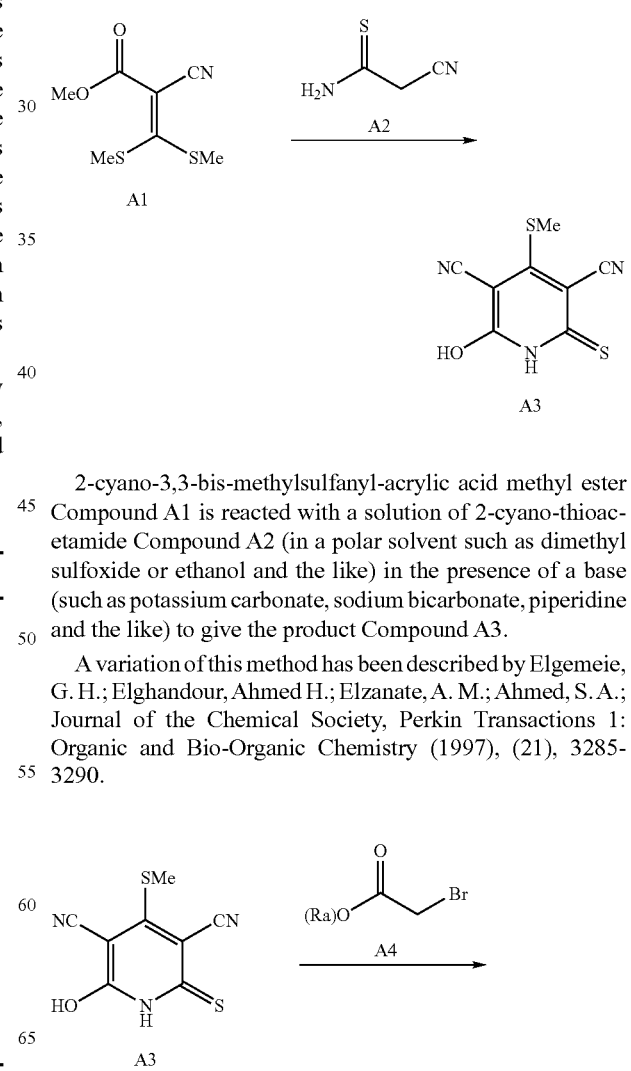

Scheme A 2-cyano-3,3-bis-methylsulfanyl-acrylic acid methyl ester Compound A1 is reacted with a solution of 2-cyano-thioacetamide Compound A2 (in a polar solvent such as dimethyl sulfoxide or ethanol and the like) in the presence of a base (such as potassium carbonate, sodium bicarbonate, piperidine and the like) to give the product Compound A3.

A variation of this method has been described by Elgemeie, G. H.; Elghandour, Ahmed H.; Elzanate, A. M.; Ahmed, S. A.; Journal of the Chemical Society, Perkin Transactions 1: Organic and Bio-Organic Chemistry (1997), (21), 3285-3290.

-continued

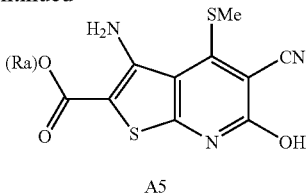

A5

A solution of Compound A3 (in a solvent such as dimethyl sulfoxide and the like) in the presence of a weak organic base (such as triethylamine, diisopropylethylamine, N-methylmorpholine and the like) is reacted with a Compound A4 (wherein Ra is as previously defined herein), then treated with a solution of potassium tert-butoxide (in a solvent such as tetrahydrofuran or tert-butanol and the like) to give a Compound A5.

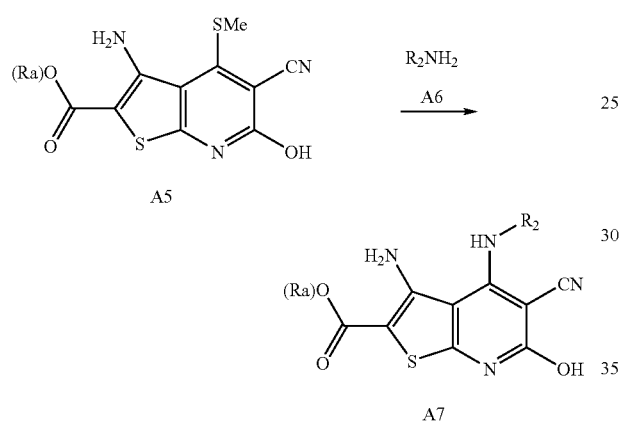

A solution of Compound A5 and an amine Compound A6 (combined in a polar aprotic solvent such as DMSO and the like) is reacted in the presence of a non-nucleophilic base such as potassium tert-butoxide or sodium hydride (in a solvent such as THF, tert-butanol, DMF and the like) to provide a Compound A7.

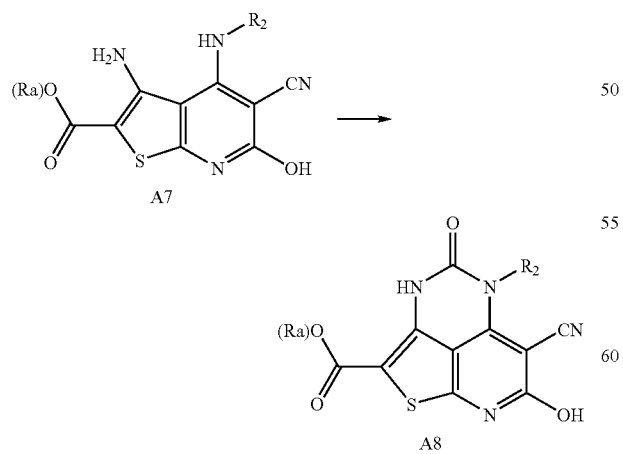

A solution of Compound A7 (in a solvent such as DMSO, THF and the like or a mixture thereof) in the presence of a non-nucleophilic base (such as potassium tert-butoxide and the like) is reacted with a carbonyl source (such as CDI, phosgene, triphosgene and the like) to provide a Compound A8, representative of a compound of Formula (I), wherein $R_1$ is —O(Ra).

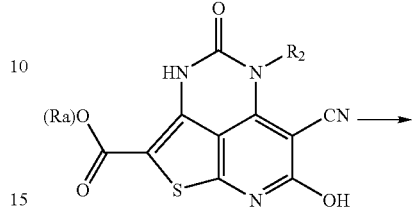

Compound A8 is treated with a halogenating reagent (such as phosphorus oxychloride) to provide a Compound A9 (wherein X is a halogen atom), representative of a compound of Formula (I), wherein $R_1$ is —O(Ra).

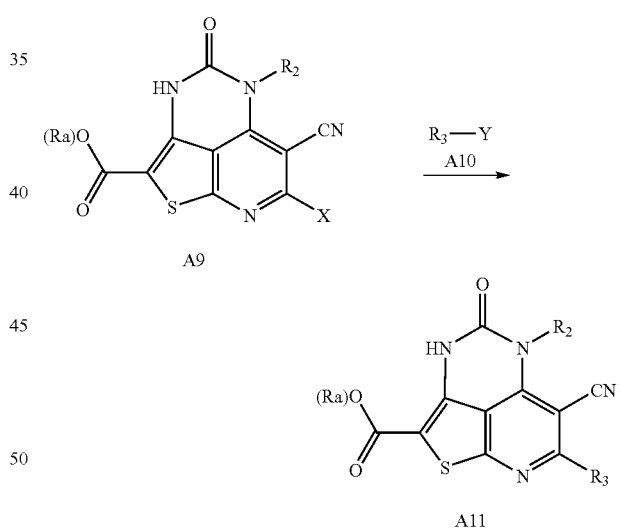

A solution of Compound A9 (in a solvent such as EtOAc, ethanol and the like) is reacted under catalytic conditions (with a catalyst such as palladium on carbon or the like) with a Compound A10 (wherein Y and $R_3$ are both hydrogen) in the optional presence of a base (such as $Et_3N$, pyridine and the like) to provide a Compound A11, representative of a compound of Formula (I), wherein $R_1$ is —O(Ra).

Alternatively, Compound A9 may be reacted under transition metal catalyzed conditions (with a catalyst such as palladium tetrakis(triphenylphosphine), palladium acetate, $PdCl_2(PPh_3)_2$ and the like) in the presence of a base (such as $K_2CO_3$, NaOtBu, NaOH, pyridine and the like) with Compound A10 (wherein the Y group for this alternative reaction sequence represents a group such as a stannane, hydrogen, boronic acid, boronic ester and the like and R₃ is as previously defined) to provide the Compound A11, representative of a compound of Formula (I), wherein R₁ is —O(Ra).

These reactions employ solvents such as toluene, DME, 1,4-dioxane, water and the like and may require additives such as phosphine ligands and copper salts.

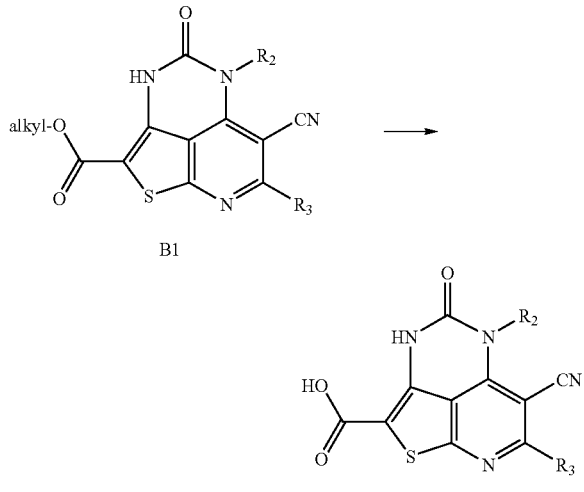

A solution of Compound B1 (in a solvent such as methanol, ethanol and the like, representative of a compound of Formula (I), wherein R₁ is —O(Ra) and Ra is alkyl) is reacted with a basic solution (such as 1N NaOH and the like in a solvent such as methanol or ethanol and the like) to give Compound B2, representative of a compound of Formula (I), wherein R₁ is —O(Ra) and Ra is hydrogen.

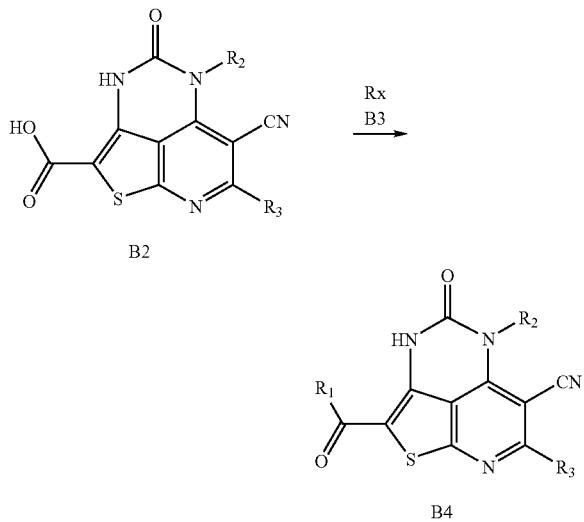

Compound B2 is reacted with a Compound B3 (using a coupling reagent such as HATU, PyBOP and the like; wherein Rx represents NH(Ra,Rb), NH(Ra,Rb) wherein Ra and Rb are taken together with the nitrogen of attachment to form a heterocyclyl ring and NH(Ra)—(CH₂)ₚ—Ar¹) to give a Compound B4, representative of a compound of Formula (I), wherein R₁ is selected from —N(Ra,Rb), —N(Ra,Rb) wherein Ra and Rb are taken together with the nitrogen of attachment to form a heterocyclyl ring and —N(Ra)—(CH₂)ₚ—Ar¹.

Alternatively, Compound B2 is treated with a reagent (such as thionyl chloride, oxalyl chloride and the like), then reacted with a solution of Compound B3 (in a solvent such as THF, DCM and the like) in the presence of a base (such as DIPEA and the like) to give a Compound B4, representative of a compound of Formula (I), wherein R₁ is selected from —N(Ra,Rb), —N(Ra,Rb) wherein Ra and Rb are taken together with the nitrogen of attachment to form a heterocyclyl ring and —N(Ra)—(CH₂)ₚ—Ar¹.

EXAMPLE 1

5-(5-chloro-benzo[1,3]dioxol-4-yl)-6-cyano-4-oxo-4,5-dihydro-3H-1-thia-3,5,8-triaza-acenaphthylene-2-carboxylic acid {4-[2-(4-methyl-piperazin-1-yl)-ethyl]-phenyl}-amide (Cpd 12)

5-(5-chloro-benzo[1,3]dioxol-4-yl)-6-cyano-4-oxo-4,5-dihydro-3H-1-thia-3,5,8-triaza-acenaphthylene-2-carboxylic acid ethyl ester (Cpd 17)

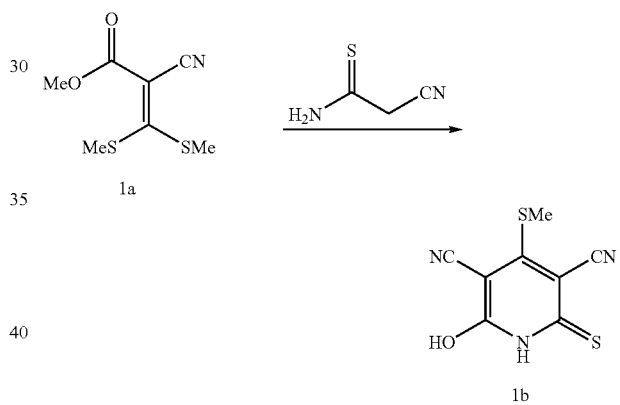

2-cyano-3,3-bis-methylsulfanyl-acrylic acid methyl ester Compound 1a (25.0 g, 123 mmol) was combined with 97% 2-cyano-thioacetamide (12.7 g, 123 mmol) and K₂CO₃ (51.0 g, 369 mmol) in DMSO (300 mL) at room temperature. The reaction was stirred for 18 hrs. The cooled reaction mixture (0° C.) was slowly acidified with 1N HCl. The resultant yellow precipitate was collected by filtration and sequentially washed with 1N HCl, water, MeOH and hexane to give 6-hydroxy-4-methylsulfanyl-2-thioxo-1,2-dihydro-pyridine-3,5-dicarbonitrile Compound 1b (24.7 g, 90% yield). ¹H NMR (DMSOd₆) δ 2.66 (s, 3H). ¹³C NMR (DMSOd₆) δ 118.1 (CN), 117.3 (CN), 17.4 (SMe). MS 222 (M⁻).

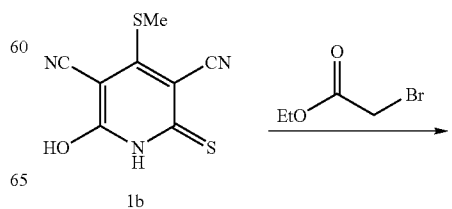

-continued

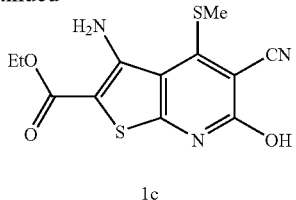

Bromo-acetic acid ethyl ester (also referred to as ethyl bromoacetate) (4.91 mL, 44.4 mmol) was added dropwise to a mixture of Compound 1b (9.90 g, 44.4 mmol) and triethylamine (6.19 mL, 44.4 mmol) in DMSO (100 mL). After 30 mins, the reaction was cooled to 10° C. and 1M KOtBu in THF (60 mL) was added dropwise. After 45 mins, the reaction was diluted with 1N HCl and filtered. The collected yellow solid was washed with 1N HCl, water, MeOH and hexane to give 3-amino-5-cyano-6-hydroxy-4-methylsulfanyl-thieno[2,3-b]pyridine-2-carboxylic acid ethyl ester Compound 1c (11.1 g). $^1$H NMR (DMSOd$_6$) δ 7.28 (br s, 2H), 4.23 (q, 2H), 2.73 (s, 3H), 1.28 (t, 3H). MS 308 (M$^−$).

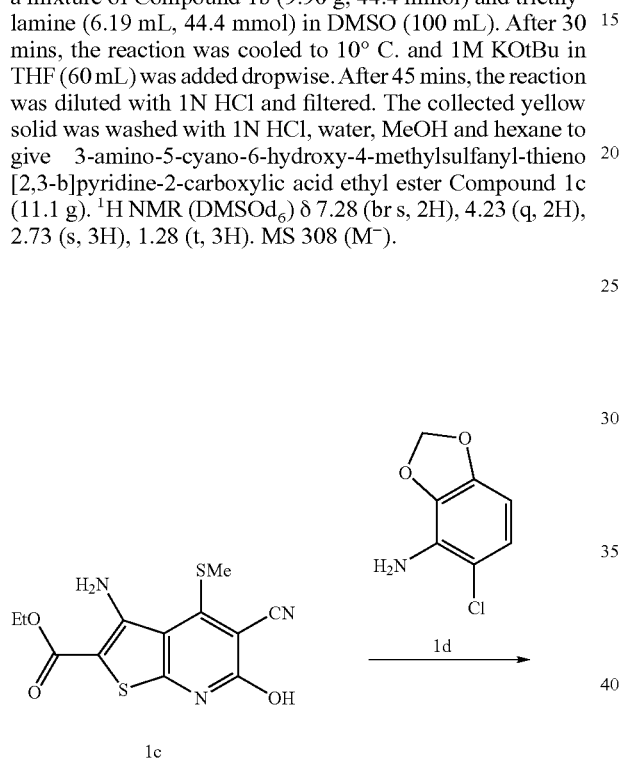

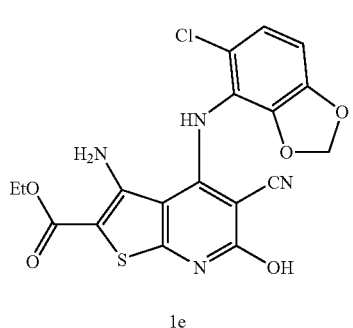

1M KOtBu (92.1 mL) was added dropwise to 5-chloro-benzo[1,3]dioxol-4-ylamine hydrochloride salt Compound 1d (6.36 g, 30.7 mmol) in DMSO (100 mL). After 30 mins, a solution of Compound 1c (8.80 g, 28.5 mmol) in DMSO (90 mL) was added to the reaction mixture. The reaction was stirred for 18 hrs and 1N HCl was added to provide a precipitate. The solid was collected and washed with 0.5 N NaH$_2$PO$_4$, MeOH and hexane to give 3-amino-4-(5-chloro-benzo[1,3]dioxol-4-ylamino)-5-cyano-6-hydroxy-thieno[2,3-b]pyridine-2-carboxylic acid ethyl ester Compound 1e (8.81 g). $^1$H NMR (DMSOd$_6$) δ 7.25 (br s, 2H), 7.03 (d, 1H), 6.95 (d, 1H), 6.14 (s, 2H), 4.23 (q, 2H), 1.28 (t, 3H). MS 433, 435 (MH$^+$).

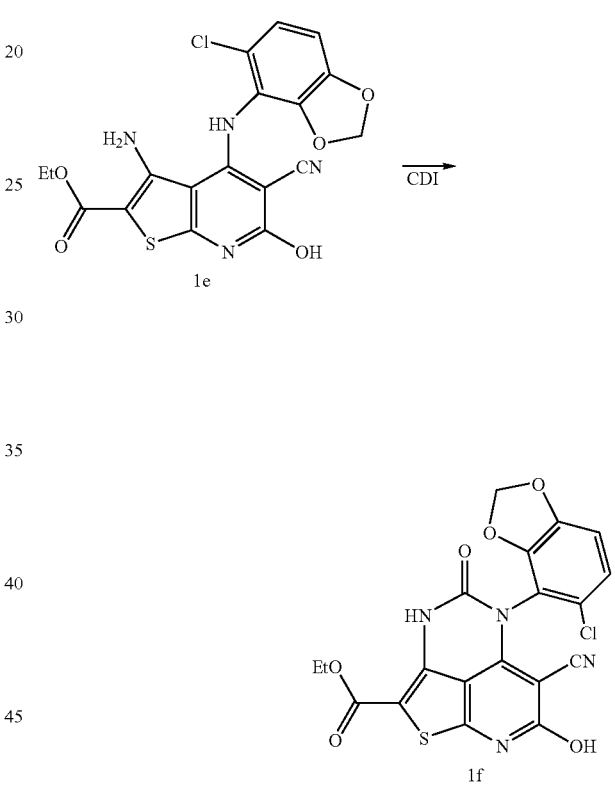

1M KOtBu (41.7 mL) was added dropwise to Compound 1e (6.02 g, 13.9 mmol) in DMSO (150 mL) and stirred for 1 hr. CDI (10.0 g, 61.6 mmol) was then added in one portion. Reaction progress was monitored by HPLC. After 18 hrs, the reaction was diluted with EtOAc and 1N HCl and filtered. The filtrate cake was rinsed and the mother liquor was extracted with EtOAc. The organic layer was dried (MgSO$_4$), then filtered and evaporated to give 5-(5-chloro-benzo[1,3]dioxol-4-yl)-6-cyano-7-hydroxy-4-oxo-4,5-dihydro-3H-1-thia-3,5,8-triaza-acenaphthylene-2-carboxylic acid ethyl ester Compound 1f (5.94 g). $^1$H NMR (DMSOd$_6$) δ 7.18 (d, 1H), 7.13 (d, 1H), 6.20 (s, 2H, rotomers), 4.31 (q, 2H), 1.30 (t, 3H). LC/MS 459, 461 (MH$^+$).

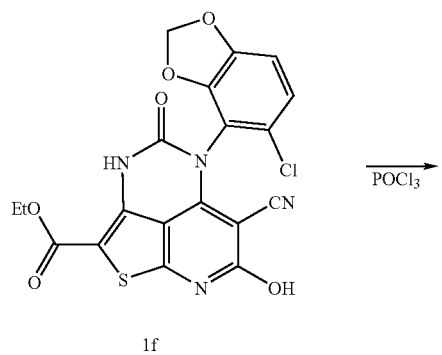

1f

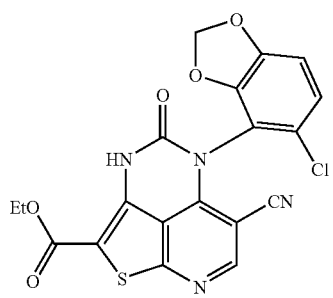

Cpd 17

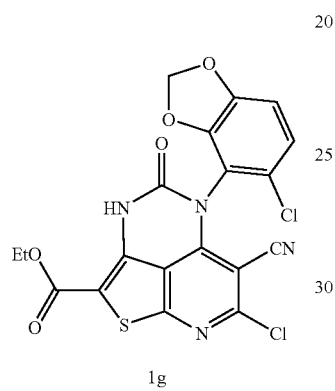

1g

A mixture of Compound 1g (1.70 g, 3.57 mmol) in pyridine (5 mL) and EtOAc (50 mL) was combined with 10% Pd/C (6.8 g) in a Parr shaker and reacted under 40 PSI hydrogen for 2 hrs. The product was filtered through Celite 545 and evaporated to give Compound 17 (1.56 g) as a yellow solid. $^1$H NMR (DMSOd$_6$) δ 8.82 (s, 1H), 7.22 (d, 1H), 7.19 (d, 1H), 6.22 (s, 2H, rotomers), 4.39 (q, 2H), 1.33 (t, 3H). LC/MS 443, 445 (MH$^+$).

Compound 1f (2.6 g, 5.68 mmol) was combined with phosphorus oxychloride (40 mL) in sealed microwave reactor vials and heated to 200° C. for 1 hr. The reaction mixture was slowly added to ice water and then extracted with EtOAc. The organic layer was washed with sat'd NaHCO$_3$, then dried over MgSO$_4$ and evaporated. The resultant solid was recrystallized from EtOAc/hexane to give 7-chloro-5-(5-chloro-benzo[1,3]dioxol-4-yl)-6-cyano-4-oxo-4,5-dihydro-3H-1-thia-3,5,8-triaza-acenaphthylene-2-carboxylic acid ethyl ester Compound 1g (2.19 g). $^1$H NMR (DMSOd$_6$) δ 7.21 (d, 1H), 7.18 (d, 1H), 6.23 (s, 2H, rotomers), 4.39 (q, 2H), 1.32 (t, 3H). LC/MS 477, 479, 481 (MH$^+$).

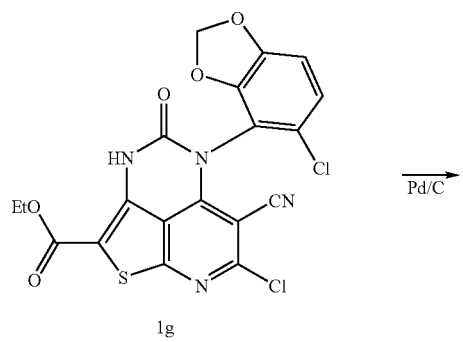

1g

Cpd 17

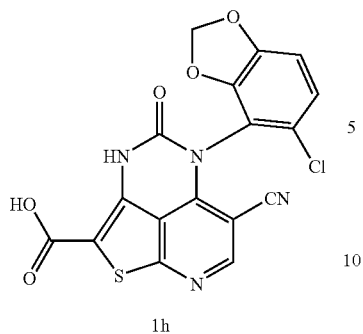

Compound 17 (1.24 g, 2.81 mmol) was refluxed for 2 hrs in 1N NaOH (10 mL) and EtOH (50 mL). The reaction was cooled to RT and partitioned between 1N HCl and EtOAc. The aqueous layer was extracted with EtOAc, dried (MgSO$_4$) and evaporated, then precipitated from EtOAc/MeOH to provide 5-(5-chloro-benzo[1,3]dioxol-4-yl)-6-cyano-4-oxo-4,5-dihydro-3H-1-thia-3,5,8-triaza-acenaphthylene-2-carboxylic acid Compound 1h (732 mg). LC/MS 415, 417 (MH$^+$).

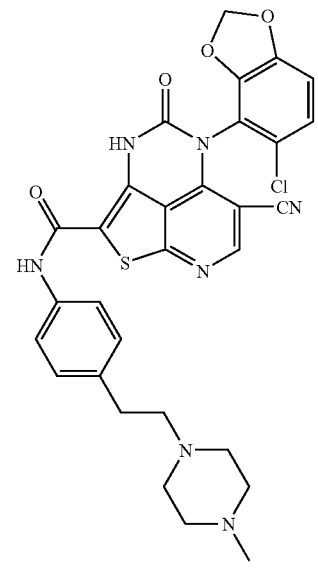

Compound 1h (152 mg, 0.367 mmol) was refluxed in thionyl chloride (5 mL) for 1 hr. The excess thionyl chloride was evaporated in vacuo and then further evaporated from DCM to provide a solid. 4-[2-(4-methyl-piperazin-1-yl)-ethyl]-phenylamine Compound 1i (80 mg, 0.367 mmol) was added to a solution of the solid in THF (5 mL) and DIPEA (0.26 mL, 1.47 mmol). After 4 hrs, the reaction mixture was diluted with sat'd NaHCO$_3$ and extracted with EtOAc. The product was dried (MgSO$_4$) and evaporated, then purified by reverse phase chromatography (C18, CH$_3$CN/water/0.05% TFA gradient) to give Compound 12 (61 mg) as a white solid. $^1$H NMR (DMSOd$_6$) δ 8.79 (s, 1H), 7.64 (d, 2H), 7.28 (d, 2H), 7.22 (d, 1H), 7.18 (d, 1H), 6.22 (s, 2H, rotomers), 4.00-2.79 (m, 12H), 2.76 (s, 3H). LC/MS 616, 618 (MH$^+$).

Using the procedure of Example 1, other representative compounds of the present invention and forms thereof may be prepared including, but not limited to:

| Cpd | Name | MS** (MH$^+$) |
|---|---|---|
| 1 | 5-(2-chloro-phenyl)-6-cyano-7-hydroxy-4-oxo-4,5-dihydro-3H-1-thia-3,5,8-triaza-acenaphthylene-2-carboxylic acid ethyl ester, | 415, 417 |
| 2 | 5-(2-chloro-phenyl)-6-cyano-4-oxo-4,5-dihydro-3H-1-thia-3,5,8-triaza-acenaphthylene-2-carboxylic acid (4-piperidin-1-ylmethyl-phenyl)-amide, | 543, 545 |
| 3 | 5-(2-chloro-phenyl)-6-cyano-4-oxo-4,5-dihydro-3H-1-thia-3,5,8-triaza-acenaphthylene-2-carboxylic acid (4-morpholin-4-ylmethyl-phenyl)-amide, | 545, 547 |

-continued

| Cpd | Name | MS** (MH+) |
|---|---|---|
| 4 | 5-(5-chloro-benzo[1,3]dioxol-4-yl)-6-cyano-4-oxo-4,5-dihydro-3H-1-thia-3,5,8-triaza-acenaphthylene-2-carboxylic acid (4-morpholin-4-ylmethyl-phenyl)-amide, | 589, 591 |
| 5 | 6-cyano-5-(2,4-dichloro-5-methoxy-phenyl)-4-oxo-4,5-dihydro-3H-1-thia-3,5,8-triaza-acenaphthylene-2-carboxylic acid (4-morpholin-4-ylmethyl-phenyl)-amide, | 609, 611 |
| 6 | 6-cyano-5-(2,4-dichloro-5-methoxy-phenyl)-4-oxo-4,5-dihydro-3H-1-thia-3,5,8-triaza-acenaphthylene-2-carboxylic acid [4-(2-morpholin-4-yl-ethyl)-phenyl]-amide, | 623, 625 |
| 10 | 5-(5-chloro-benzo[1,3]dioxol-4-yl)-6-cyano-4-oxo-4,5-dihydro-3H-1-thia-3,5,8-triaza-acenaphthylene-2-carboxylic acid (1-methyl-piperidin-4-yl)-amide, | 511, 513 |
| 11 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2-piperidin-1-yl-ethyl)-phenyl]-amide, | 601, 603 |
| 13 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2-morpholin-4-yl-ethyl)-phenyl]-amide, | 603, 605 |
| 14 | 6-cyano-7-hydroxy-4-oxo-5-pyridin-4-yl-4,5-dihydro-3H-1-thia-3,5,8-triaza-acenaphthylene-2-carboxylic acid ethyl ester, | 382, 384 |
| 18 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methoxy-piperidin-1-ylmethyl)-phenyl]-amide, | 617, 619 |
| 19 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methyl-piperidin-1-ylmethyl)-phenyl]-amide, | 601, 603 |
| 20 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3-hydroxymethyl-piperidin-1-ylmethyl)-phenyl]-amide, | 617, 619 |
| 21 | 5-(5-chloro-benzo[1,3]dioxol-4-yl)-2-(3-hydroxymethyl-piperidine-1-carbonyl)-4-oxo-4,5-dihydro-3H-1-thia-3,5,8-triaza-acenaphthylene-6-carbonitrile, | 512, 514 |
| 22 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxymethyl-piperidin-1-ylmethyl)-phenyl]-amide, | 617, 619 |
| 23 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxy-piperidin-1-ylmethyl)-phenyl]-amide, | 603, 605 |
| 24 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3,5-dimethyl-morpholin-4-ylmethyl)-phenyl]-amide, | 617, 619 |
| 25 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2,6-cis-dimethyl-morpholin-4-ylmethyl)-phenyl]-amide, | 617, 619 |
| 26 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-fluoro-piperidin-1-ylmethyl)-phenyl]-amide, | 605, 607 |
| 27 | 5-(5-chloro-benzo[1,3]dioxol-4-yl)-6-cyano-4-oxo-4,5-dihydro-3H-1-thia-3,5,8-triaza-acenaphthylene-2-carboxylic acid (3-dimethylamino-4-morpholin-4-ylmethyl-phenyl)-amide, | 632, 634 |
| 28 | 5-(5-chloro-benzo[1,3]dioxol-4-yl)-2-(4-hydroxy-piperidine-1-carbonyl)-4-oxo-4,5-dihydro-3H-1-thia-3,5,8-triaza-acenaphthylene-6-carbonitrile, | 498, 500 |
| 29 | 5-(5-chloro-benzo[1,3]dioxol-4-yl)-6-cyano-4-oxo-4,5-dihydro-3H-1-thia-3,5,8-triaza-acenaphthylene-2-carboxylic acid methyl-(4-morpholin-4-ylmethyl-phenyl)-amide, | 603, 605 |
| 30 | 5-(5-chloro-benzo[1,3]dioxol-4-yl)-6-cyano-4-oxo-4,5-dihydro-3H-1-thia-3,5,8-triaza-acenaphthylene-2-carboxylic acid [6-(3-morpholin-4-yl-propylamino)-pyridin-3-yl]-amide, | 633, 635 |
| 31 | 5-(5-chloro-benzo[1,3]dioxol-4-yl)-6-cyano-4-oxo-4,5-dihydro-3H-1-thia-3,5,8-triaza-acenaphthylene-2-carboxylic acid [3-methoxy-4-(2-piperidin-1-yl-ethoxy)-phenyl]-amide, | 647, 649 |
| 32 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(1-methyl-piperidin-2-ylmethoxy)-phenyl]-amide, | 617, 619 |
| 33 | 5-(5-chloro-benzo[1,3]dioxol-4-yl)-6-cyano-4-oxo-4,5-dihydro-3H-1-thia-3,5,8-triaza-acenaphthylene-2-carboxylic acid (1H-pyrazol-3-yl)-amide, | 480, 482 |
| 34 | 5-(5-chloro-benzo[1,3]dioxol-4-yl)-6-cyano-4-oxo-4,5-dihydro-3H-1-thia-3,5,8-triaza-acenaphthylene-2-carboxylic acid (5-methyl-isoxazol-3-yl)-amide, | 495, 497 |
| 35 | 5-(5-chloro-benzo[1,3]dioxol-4-yl)-6-cyano-4-oxo-4,5-dihydro-3H-1-thia-3,5,8-triaza-acenaphthylene-2-carboxylic acid pyrimidin-2-ylamide, | 492, 494 |
| 36 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-3-ylamide, | 491, 493 |

-continued

| Cpd | Name | MS** (MH+) |
|---|---|---|
| 37 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-2-ylamide, | 491, 493 |
| 38 | 5-(5-chloro-benzo[1,3]dioxol-4-yl)-6-cyano-4-oxo-4,5-dihydro-3H-1-thia-3,5,8-triaza-acenaphthylene-2-carboxylic acid (2-hydroxy-1,1-dimethyl-ethyl)-amide, | 486, 488 |
| 39 | 5-(5-chloro-benzo[1,3]dioxol-4-yl)-6-cyano-4-oxo-4,5-dihydro-3H-1-thia-3,5,8-triaza-acenaphthylene-2-carboxylic acid (1-methyl-1H-pyrazol-3-yl)-amide, | 494, 496 |
| 40 | 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-4-ylamide, | 491, 493 |
| 41 | 5-(5-chloro-benzo[1,3]dioxol-4-yl)-2-(4-dimethylamino-piperidine-1-carbonyl)-4-oxo-4,5-dihydro-3H-1-thia-3,5,8-triaza-acenaphthylene-6-carbonitrile, | 525, 527 |
| 42 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-dimethylamino-piperidin-1-ylmethyl)-phenyl]-amide, | 630, 632 |
| 43 | 5-(5-chloro-benzo[1,3]dioxol-4-yl)-2-(3-fluoro-piperidine-1-carbonyl)-4-oxo-4,5-dihydro-3H-1-thia-3,5,8-triaza-acenaphthylene-6-carbonitrile, | 500, 502 |
| 44 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3-fluoro-piperidin-1-ylmethyl)-phenyl]-amide, | 605, 607 |
| 45 | 6-cyano-4-oxo-5-(4-phenoxy-phenyl)-4,5-dihydro-3H-1-thia-3,5,8-triaza-acenaphthylene-2-carboxylic acid (3-methoxy-4-morpholin-4-ylmethyl-phenyl)-amide, | 633, 635 |
| 46 | [1-(4-{[5-(5-chloro-benzo[1,3]dioxol-4-yl)-6-cyano-4-oxo-4,5-dihydro-3H-1-thia-3,5,8-triaza-acenaphthylene-2-carbonyl]-amino}-benzyl)-piperidin-4-yl]-carbamic acid tert-butyl ester, | 702, 704 |
| 47 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-amino-piperidin-1-ylmethyl)-phenyl]-amide, | 602, 604 |
| 48 | 6-cyano-4-oxo-5-(4-phenoxy-phenyl)-4,5-dihydro-3H-1-thia-3,5,8-triaza-acenaphthylene-2-carboxylic acid [4-(2-piperidin-1-yl-ethyl)-phenyl]-amide, | 615, 617 |
| 49 | 6-cyano-4-oxo-5-(4-phenoxy-phenyl)-4,5-dihydro-3H-1-thia-3,5,8-triaza-acenaphthylene-2-carboxylic acid (4-piperidin-1-ylmethyl-phenyl)-amide, | 601, 603 |
| 50 | 6-cyano-4-oxo-5-(4-phenoxy-phenyl)-4,5-dihydro-3H-1-thia-3,5,8-triaza-acenaphthylene-2-carboxylic acid (4-morpholin-4-ylmethyl-phenyl)-amide, | 603, 605 |
| 51 | 6-cyano-4-oxo-5-(4-phenoxy-phenyl)-4,5-dihydro-3H-1-thia-3,5,8-triaza-acenaphthylene-2-carboxylic acid [4-(4-methoxy-piperidin-1-ylmethyl)-phenyl]-amide, | 631, 633 |
| 52 | 6-cyano-7-hydroxy-4-oxo-5-(4-phenoxy-phenyl)-4,5-dihydro-3H-1-thia-3,5,8-triaza-acenaphthylene-2-carboxylic acid ethyl ester, | 473, 475 |
| 53 | 7-chloro-6-cyano-4-oxo-5-(4-phenoxy-phenyl)-4,5-dihydro-3H-1-thia-3,5,8-triaza-acenaphthylene-2-carboxylic acid ethyl ester, or | 491, 493 |
| 54 | 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4,4-difluoro-piperidin-1-ylmethyl)-phenyl]-amide. | 623, 625 |

**The two numbers for the MH+ is due to the fact that the molecules contain chlorine and the chlorine has two isotopes with substantial abundance, i.e. $^{35}$Cl and $^{37}$Cl.

EXAMPLE 2

5-(5-chloro-benzo[1,3]dioxol-4-yl)-6-cyano-7-methyl-4-oxo-4,5-dihydro-3H-1-thia-3,5,8-triaza-acenaphthylene-2-carboxylic acid (4-morpholin-4-ylmethyl-phenyl)-amide (Cpd 9)

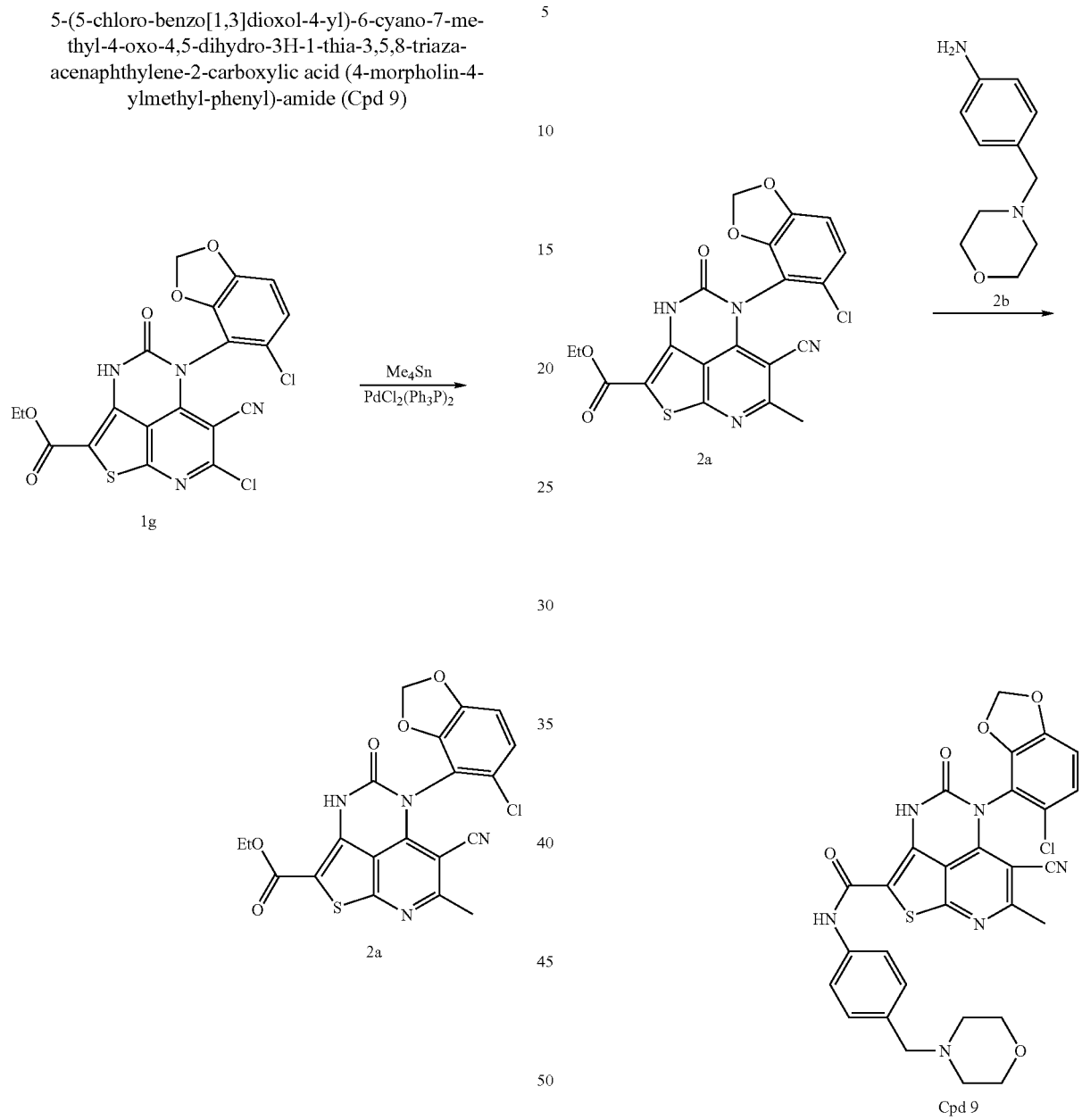

7-chloro-5-(5-chloro-benzo[1,3]dioxol-4-yl)-6-cyano-4-oxo-4,5-dihydro-3H-1-thia-3,5,8-triaza-acenaphthylene-2-carboxylic acid ethyl ester Compound 1g (115 mg, 0.242 mmol) was combined with 95% tetramethyltin (0.039 ml, 0.266 mmol), PdCl$_2$(Ph$_3$P)$_2$ (17 mg, 0.024 mmol) and DMF (3 mL) in a sealed microwave vessel. The mixture was heated to 150° C. for 15 mins. The reaction mixture was diluted with 0.5 M NaH$_2$PO$_4$ and extracted with EtOAc, then dried (MgSO$_4$) and evaporated. The resulting residue was purified by flash chromatography (30 to 50% EtOAc/hexane/1% Et$_3$N) to give 5-(5-chloro-benzo[1,3]dioxol-4-yl)-6-cyano-7-methyl-4-oxo-4,5-dihydro-3H-1-thia-3,5,8-triaza-acenaphthylene-2-carboxylic acid ethyl ester Compound 2a (57 mg) as a white solid. LC/MS 457 (MH$^+$).

Using the procedure of Example 1, Compound 2a was used in place of Compound 17 and carried forward, then 4-morpholin-4-ylmethyl-phenylamine Compound 2b was used in place of 4-[2-(4-methyl-piperazin-1-yl)-ethyl]-phenylamine Compound 1i to give Compound 9 as an off-white solid. $^1$H NMR (DMSOd$_6$) δ 10.38 (s, 1H), 10.0 (br s, 1H), 7.79 (d, 2H), 7.49 (d, 2H), 7.20 (d, 1H), 7.15 (d, 1H), 6.21 (s, 2H, rotomers), 4.32 (s, 2H), 4.09-3.00 (m, 8H), 2.65 (s, 3H). LC/MS 603, 605 (MH$^+$).

EXAMPLE 3

7-(2-chloro-5-fluoro-phenyl)-6-cyano-4-oxo-5-pyridin-4-yl-4,5-dihydro-3H-1-thia-3,5,8-triaza-acenaphthylene-2-carboxylic acid ethyl ester (Cpd 15)

7-(2-chloro-5-fluoro-phenyl)-6-cyano-4-oxo-5-pyridin-4-yl-4,5-dihydro-3H-1-thia-3,5,8-triaza-acenaphthylene-2-carboxylic acid (2-pyrrolidin-1-yl-ethyl)-amide (Cpd 16)

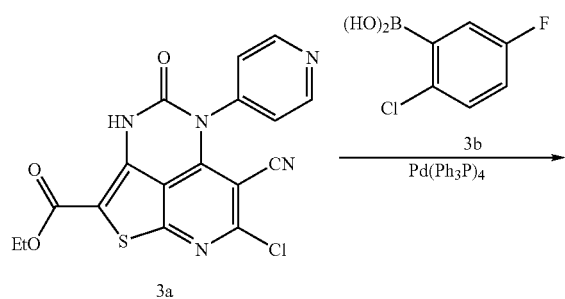

7-chloro-6-cyano-4-oxo-5-pyridin-4-yl-4,5-dihydro-3H-1-thia-3,5,8-triaza-acenaphthylene-2-carboxylic acid ethyl ester Compound 3a (537 mg, 1.35 mmol), prepared using the procedure of Example 1, was combined with 2-chloro-5-fluorophenyl-boronic acid (468 mg, 2.69 mmol), Pd(Ph$_3$P)$_4$ (156 mg, 0.135 mmol), sat'd NaHCO$_3$ (15 mL) and 1,4-dioxane (40 mL). The reaction mixture was refluxed for 2 hrs then diluted with sat'd NaHCO$_3$ and extracted with EtOAc. The organic layer was dried (MgSO$_4$) and evaporated. The solid was recrystallized from EtOAc to give 7-(2-chloro-5-fluoro-phenyl)-6-cyano-4-oxo-5-pyridin-4-yl-4,5-dihydro-3H-1-thia-3,5,8-triaza-acenaphthylene-2-carboxylic acid ethyl ester Compound 15 (440 mg) as a pale yellow solid. LC/MS 494, 496 (MH$^+$).

Compound 15 (394 mg, 0.80 mmol) was refluxed for 2 hrs in 1N NaOH (5 mL), THF (5 mL) and EtOH (5 mL). The reaction mixture was cooled to RT and diluted with 0.5 M NaH$_2$PO$_4$ to provide a precipitate, which was collected and used without further purification. LC/MS 466, 468 (MH$^+$). The crude solid (67 mg, 0.144 mmol) was combined with HATU (66 mg, 0.173 mmol) in THF (3 mL) and stirred for 30 mins.

DIPEA (0.03 ml, 0.173 mmol) and 2-pyrrolidin-1-yl-ethylamine Compound 3c (20 mg, 0.173 mmol) were added to the reaction mixture. After 4 hrs, the reaction was diluted with 1M NaOH and extracted with EtOAc, then dried (MgSO$_4$) and evaporated. The crude product was purified by reverse phase chromatography (C18, CH$_3$CN/water/0.05% TFA gradient) to give Compound 16 (3 mg) as a white solid. LC/MS 562, 564 (MH$^+$).

EXAMPLE 4

5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid ethyl ester (Cpd 7)

5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid (4-morpholin-4-ylmethyl-phenyl)-amide (Cpd 8)

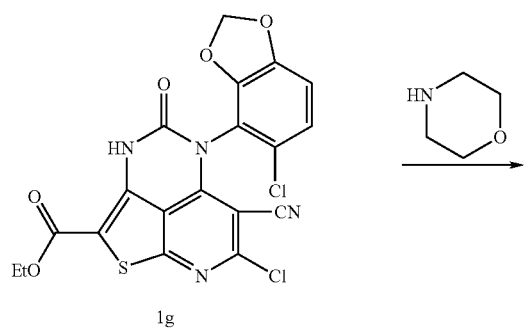

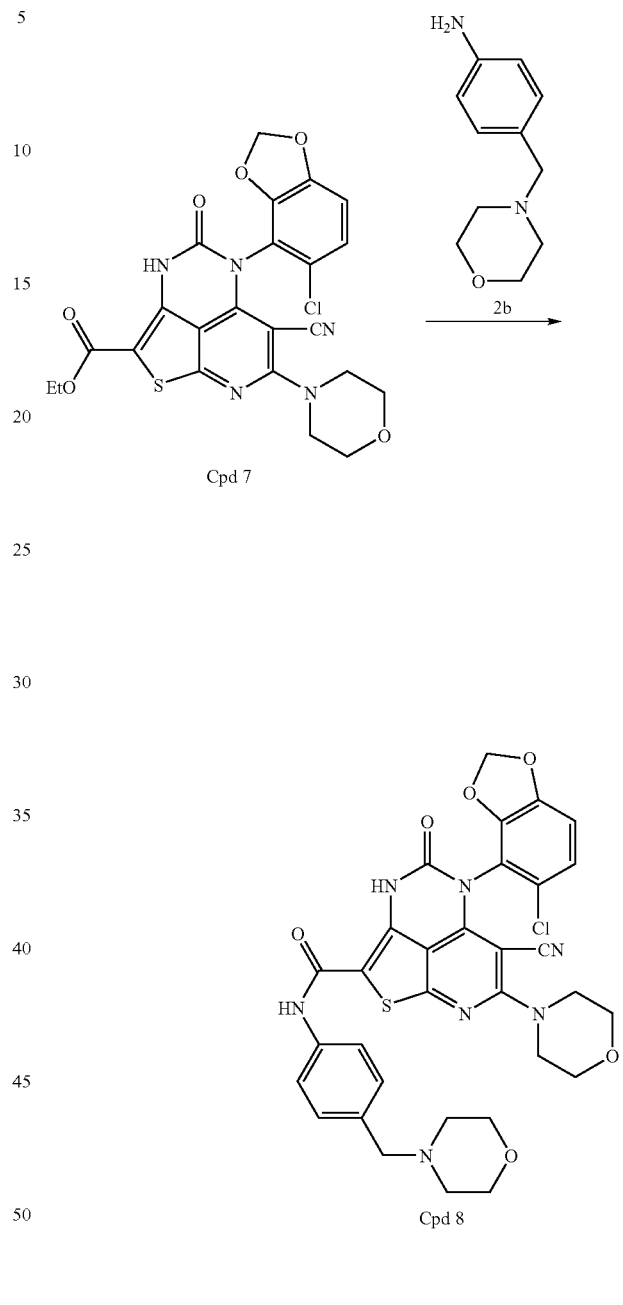

Compound 1g (108 mg, 0.227 mmol) was combined with morpholine (0.040 ml, 0.454 mmol) and EtOH (3 mL) in a sealed microwave vial. The mixture was heated in a microwave at 120° C. for 15 mins. The reaction mixture was diluted with 0.5 M $NaH_2PO_4$ and the precipitate collected by filtration. The crude solid was washed with MeOH and hexane to give Compound 7(89 mg). $^1$H NMR (DMSOd$_6$) δ 11.28(s, 1H), 7.16 (d, 1H), 7.14 (d, 1H), 6.19 (s, 2H, rotomers), 4.33 (q, 2H), 3.70-3.63 (m, 4H), 3.48-3.43 (m, 4H), 1.30 (t, 3H). LC/MS 528, 530 (MH$^+$).

Using the procedure of Example 1, Compound 7 was used in place of Compound 17 and carried forward, then 4-morpholin-4-ylmethyl-phenylamine Compound 2b was used in place of 4-[2-(4-methyl-piperazin-1-yl)-ethyl]-phenylamine Compound 1i to give Compound 8 as an off-white TFA salt. $^1$H NMR (DMSOd$_6$) δ 10.23(s, 1H), 9.92 (br s, 1H), 7.78 (d, 2H), 7.48 (d, 2H), 7.17 (d, 1H), 7.14 (d, 1H), 6.20 (s, 2H, rotomers), 4.30 (br s, 2H), 4.08-3.88 (m, 2H), 3.73-3.02 (m, 14H). LC/MS 674, 676 (MH$^+$).

BIOLOGICAL EXAMPLES

The usefulness of the compounds of the present invention for treating, preventing or ameliorating a chronic or acute kinase mediated disease, disorder or condition was determined using the following procedures.

Examples 6 and 8 are intended as prophetic examples and are expected to demonstrate that said compounds are useful in treating, preventing or ameliorating a chronic or acute kinase mediated disease, disorder or condition as an inhibitor of the indicated kinase.

Example 1

EGFR Kinase Assay

The EGFR kinase used was a fusion of Glutathione-S-Transferase (GST) and a PCR amplified intracellular portion of EGFR (NM_005228). The intracellular portion of EGFR started at nucleotide 2189 (corresponding to amino acid 667) and ended at the termination codon. The portion was PCR amplified with primers that added the lambda attB sequences to each end, recombined into an entry vector, then into a GST destination vector (as described in Gateway Technologies Manual by Invitrogen Corporation, Carlsbad, Calif.).

The destination vector was recombined in the DH10BAC strain of bacteria to produce a bacmid. The bacmid was transfected into Sf 9 cells and the supernatant containing the baculovirus was collected. The GSTEGFR protein was purified using large cultures of Sf 9 cells infected with stock virus. After an appropriate period of time, the cells were collected and lysed. The GSTEGFR was then purified from the lysate on Glutathione-Sepharose columns (as described by Amersham Biosciences, Buckinghamshire, United Kingdom).

The EGFR substrate was prepared by biotinylating polyGluTyr (128 mg) (Sigma, St. Louis, Mo.) in a 1×PBS buffer incubated together with a 12-fold molar excess of Sulfo-NHS-LC-Biotin on ice for at least 2 hrs. The free biotin was separated from the biotinylated polyGluTyr on a gel filtration column.

A mixture of a 10× kinase buffer (500 mM Tris at pH 8.0, 100 mM Magnesium Chloride and 1 mM Sodium Vanadate), DTT (1 mM final from 500 mM stock), ATP (5 µM final from 10 mM stock), biotinylated polyGluTyr (10 µg/µL stock), γ-$^{33}$P ATP (10 µCi/µL stock) and water was added to each well (90 µL/well) of a Streptavidin Flashplate (Perkin Elmer, Wellesley, Mass.).

Test compound in 100% DMSO (2 µL) was added to the appropriate wells. Diluted GSTEGFR (1:300 dilution in 50 mM Tris at pH 8.0 and 0.1% bovine serum albumin) (10 µL) was added to the wells to initiate the reactions.

The plates were incubated at 30° C. for 1 hr with shaking. The reacted contents were removed and the plates were sequentially washed three times with a 1×PBS stop buffer (300 µL without Magnesium and Calcium) and 100 mM EDTA. After the final wash, the same stop buffer (200 µL) was added to the wells. The plates were then sealed and read on the TopCount scintillation counter.

Test compounds were assayed in triplicate at 16 concentrations at half-log dilutions starting at 200 uM. A maximum and minimum signal for the assay was determined on each plate. The percent inhibition of a test compound was calculated according to the formula $$\left[\frac{(\text{max signal} - \text{test compound})}{(\text{max signal} - \text{min signal})}\right](100) = \% \text{ inhibition}$$

For a series of test concentrations, the IC$_{50}$ was derived by graphing percent inhibition against the log of the concentrations tested for a given compound. The IC$_{50}$ results are shown in Table 1. For those compounds without an IC$_{50}$, the percent inhibition results are shown at a test concentration of 2 µM.

TABLE 1

| Cpd | EGFR IC$_{50}$ (µM) IC$_{50}$ (avg) |
|---|---|
| 2 | 1.67 |
| 3 | 2.21 |
| 4 | 36% |
| 5 | 1% |
| 6 | 7% |
| 7 | −5% |
| 8 | −6% |
| 9 | 14% |
| 10 | 3.96 |
| 11 | 1.60 |
| 12 | 2.70 |
| 13 | 23% |
| 14 | −9% |
| 15 | 6% |
| 18 | 38% |
| 19 | 0.624 |
| 20 | 0.910 |
| 21 | 32% |
| 22 | 0.567 |
| 23 | 0.598 |
| 24 | 24% |
| 25 | 24% |
| 26 | 2.02 |
| 27 | 34% |
| 28 | 9% |
| 29 | 2% |
| 30 | 11% |
| 31 | 0.513 |
| 32 | 35% |
| 33 | 1.22 |
| 34 | 30% |
| 35 | 42% |
| 36 | 35% |
| 37 | 10% |
| 38 | 13% |
| 39 | 26% |
| 40 | 30% |
| 41 | 7% |
| 42 | 0.850 |
| 45 | 0.093 |
| 46 | 0.152 |
| 47 | 0.514 |
| 48 | 39% |
| 49 | 0.224 |
| 50 | 0.124 |
| 51 | 48% |
| 52 | 0.0169 |
| 53 | 2% |
| 54 | 11% |

Example 2

VEGF-R2 and Aurora-A Screening Assays

A kinase reaction mixture was prepared containing 50 mM Tris-HCl at pH 8, 10 mM, MgCl$_2$ 0.1 mM Na$_3$PO$_4$, 1 mM DTT, 10 µM ATP, 0.025 µM biotinylated histone-H1 peptide substrate and 0.2 µCuries per well $^{33P}$-γ-ATP (2000-3000

Ci/mmol). 70 μL of the kinase reaction mixture was dispensed into the well of a Streptavidin FlashPlate.

Test compound stock in 100% DMSO (1 μL) was added to the wells resulting in a final concentration of 1% DMSO in the reaction with a 100 μL final reaction volume. Each enzyme was diluted in 50 mM Tris-HCl pH=8.0, 0.1% BSA and 30 μL was added to each well to initiate the reaction. The reaction was incubated for one hour at 30° C. At the end of the 1 hr incubation, the reaction was terminated by aspirating the mixture from the plate and washing the wells twice with PBS containing 100 mM EDTA. The biotinylated peptide substrate became immobilized on the Flashplate[198] and the incorporation of $^{33}$P-γ-ATP was measured by reading the plate on a scintillation counter. Inhibition of the enzymatic activity was measured by observing a reduced amount of $^{33}$P-γ-ATP incorporated into the immobilized peptide.

The VEGF-R2 enzyme is a fusion protein containing a polyhistidine tag at the N terminus followed by amino acids 786 to 1343 of the rat VEGF-R2 kinase domain (Accession number U93306). The assay used 150 ng of the N-terminal biotinylated peptide biotin-KHKKLAEGSAYEEV-amide (VEGF-R2) per well.

Aurora-A is a fusion protein containing a polyhistidine tag at the N terminus followed by the full length protein encoding the murine Aurora-A (Accession number GB BC014711) expressed and purified from sf9 insect cells. The assay used 400 ng of the N-terminal biotinylated peptide biotin-GRT-GRRNSI-amide (Aurora-A) per well.

The IC$_{50}$ was derived according to the procedure described in Example 2. The IC$_{50}$ results for VEGF-R2 are shown in Table 2A and the IC$_{50}$ results for Aurora-A are shown in Table 2B. For those compounds without an IC$_{50}$, the percent inhibition results are shown at a test concentration of 1 μM.

TABLE 2A

VEGF-R2 IC$_{50}$ (μM)

| Cpd | IC$_{50}$ (avg) |
|---|---|
| 2 | >100 |
| 3 | >100 |
| 4 | >10 |
| 5 | >100 |
| 6 | >100 |
| 7 | >100 |
| 8 | 14.1 |
| 9 | >10 |
| 10 | ~100 |
| 11 | >100 |
| 12 | >100 |
| 13 | >10 |
| 14 | >100 |
| 15 | >100 |
| 18 | >10 |
| 19 | >100 |
| 20 | 24% |
| 21 | >100 |
| 22 | >100 |
| 23 | 28% |
| 24 | 14% |
| 25 | 0% |
| 26 | 11% |
| 27 | 7% |
| 28 | 15% |
| 29 | 10% |
| 30 | 12% |
| 31 | 17% |
| 32 | 1% |
| 33 | 18% |
| 34 | 16% |
| 35 | 22% |
| 36 | 15% |

TABLE 2A-continued

VEGF-R2 IC$_{50}$ (μM)

| Cpd | IC$_{50}$ (avg) |
|---|---|
| 37 | −22% |
| 38 | 2% |
| 39 | 9% |
| 40 | 9% |
| 41 | >100 |
| 42 | >100 |
| 43 | ~100 |
| 44 | >10 |
| 45 | >100 |
| 46 | >100 |
| 47 | >100 |
| 48 | >100 |
| 49 | >100 |
| 50 | >10 |
| 51 | >100 |
| 52 | >100 |
| 53 | >100 |
| 54 | 12.3 |

TABLE 2B

Aurora-A IC$_{50}$ (μM)

| Cpd | IC$_{50}$ (avg) |
|---|---|
| 2 | 10.7 |
| 3 | >10 |
| 4 | 10.6 |
| 5 | >10 |
| 6 | >10 |
| 7 | >10 |
| 8 | 6.47 |
| 9 | >1 |
| 10 | 13.3 |
| 11 | >1 |
| 12 | ~10 |
| 13 | 5.93 |
| 14 | >100 |
| 15 | >100 |
| 18 | >1 |
| 19 | 9% |
| 20 | 21% |
| 21 | 3% |
| 22 | 15% |
| 23 | 16% |
| 24 | 7% |
| 25 | 18% |
| 26 | 23% |
| 27 | 16% |
| 28 | 25% |
| 29 | 13% |
| 30 | 22% |
| 31 | 22% |
| 32 | 13% |
| 33 | 29% |
| 34 | 29% |
| 35 | 16% |
| 36 | 21% |
| 37 | 3% |
| 38 | 4% |
| 39 | 15% |
| 40 | 15% |
| 41 | >10 |
| 42 | >10 |
| 43 | >10 |
| 44 | 1.1 |
| 45 | >100 |
| 46 | >1 |
| 47 | >100 |
| 48 | >100 |
| 49 | >100 |
| 50 | >100 |

TABLE 2B-continued

| Aurora-A IC$_{50}$ (μM) | |
| --- | --- |
| Cpd | IC$_{50}$ (avg) |
| 51 | >100 |
| 52 | >100 |
| 53 | >100 |
| 54 | 15.3 |

Example 3

HER-2 Kinase Assay

HER-2 kinase was purified at Proqinase (Freiburg, Germany) from a construct that consisted of a fusion of GST (Glutathione-S-Transferase), HIS6-Thrombin and the nucleotides encoding amino acids 679 to 1255 of HER-2.

A mixture of a 10× kinase reaction buffer (600 mM Hepes at pH 7.5, 30 mM Magnesium Chloride, 0.03 mM Sodium Vanadate and 500 μg/mL PEG 20,000), DTT (1.2 mM final from a 10 mM stock), ATP (1 μM from a 10 mM stock), biotinylated polyGluTyr (1.5 ng/μL final from stock of 1 μg/μL prepared by Upstate Biotechnologies, Lake Placid, N.Y.), Manganese Chloride (3 mM final from a 1 M stock), γ-$^{33}$P-ATP (10 μCi/μL stock) and water (70 μL/well) was added to each well of a Streptavidin Flashplate (Cat. #SMP103, NEN, Boston, Mass.).

Test compound stock (1 μL) was added to the appropriate wells. Diluted GSTHER2 kinase (6.7 ng/μL diluted into 50 mM Tris-HCl at pH 8.0 and 0.1% bovine serum albumin) (30 μL) was added (total volume of 200 ng/well) to initiate the reactions.

The reaction plates were incubated at 30° C. for 1 hr. The reaction was terminated by aspirating the reaction mixture from the plate wells and washing the wells three times with a 1×PBS stop buffer (300 μL) and 100 mM EDTA. After the final wash, the same stop buffer (200 μL) was again added to the wells. The plates were then sealed and read on the TopCount scintillation counter.

The IC$_{50}$ was derived according to the procedure described in Example 2. The IC$_{50}$ results for HER-2 are shown in Table 3. For those compounds without an IC$_{50}$, the percent inhibition results are shown at a test concentration of 1 μM.

TABLE 3

| HER-2 IC$_{50}$ (μM) | |
| --- | --- |
| Cpd | IC$_{50}$ (avg) |
| 2 | 3.46 |
| 3 | 4.10 |
| 4 | 5.35 |
| 5 | >10 |
| 6 | ~100 |
| 7 | >100 |
| 8 | ~100 |
| 9 | >10 |
| 10 | 7.16 |
| 11 | 2.91 |
| 12 | 5.55 |
| 13 | >1 |
| 14 | >100 |
| 15 | >100 |
| 18 | 1.23 |
| 19 | 49% |
| 20 | 41% |
| 21 | 13% |

TABLE 3-continued

| HER-2 IC$_{50}$ (μM) | |
| --- | --- |
| Cpd | IC$_{50}$ (avg) |
| 22 | 48% |
| 23 | 44% |
| 24 | 12% |
| 25 | 3% |
| 26 | >1 |
| 27 | 0% |
| 28 | 35% |
| 29 | 0% |
| 30 | 35% |
| 31 | 35% |
| 32 | 22% |
| 33 | 37% |
| 34 | >1 |
| 35 | >1 |
| 36 | 29% |
| 37 | 11% |
| 38 | 0% |
| 39 | 0% |
| 40 | 0% |
| 41 | 13.5 |
| 42 | >1 |
| 43 | 10.6 |
| 44 | 1.1 |
| 45 | 0.0836 |
| 46 | 0.134 |
| 47 | 1.87 |
| 48 | >10 |
| 49 | 0.836 |
| 50 | 2.20 |
| 51 | >10 |
| 52 | >10 |
| 53 | >100 |
| 54 | 3.37 |

Example 4 c-Src Kinase Assay

A mixture of a 10× kinase buffer (80 mM MOPS at pH 7.0, 2 mM EDTA and 100 mM Magnesium Chloride), ATP (5 μM final from a 10 mM stock), a Cdc2 peptide KVEKIGEGTYV-VYK (100 μM final from a 2.5 mM stock), γ-$^{33}$P ATP (10 μCi/μL stock) and water (20 μL/well) was added to each well of a Streptavidin Flashplate.

Test compound in 100% DMSO (0.5 μL) was added to the appropriate wells. Diluted c-Src kinase (human) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%) and 1 mg/mL bovine serum albumin) (2.5 μL) was added to the wells to initiate the reactions. The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

Percent inhibition was derived according to the procedure described in Example 2. The IC$_{50}$ results for c-Src are shown in Table 4. For those compounds without an IC$_{50}$, the percent inhibition results are shown at a test concentration of 2 μM.

TABLE 4 c-Src IC$_{50}$ (μM)

| Cpd | IC$_{50}$ (avg) |
|---|---|
| 2 | 3.12 |
| 3 | 30% |
| 4 | 0.0574 |
| 5 | 0.355 |
| 6 | 0.368 |
| 7 | −1% |
| 8 | −21% |
| 9 | 11% |
| 10 | 0.0870 |
| 11 | 0.0712 |
| 12 | 91% |
| 13 | 78% |
| 14 | 11% |
| 15 | −0.6% |
| 19 | 90% |

Example 5

Lyn Kinase Assay

A mixture of a 10× kinase buffer (500 mM MOPS at pH 7.5, 1 mM EGTA, 1 mM Sodium Vanadate, 1% β-mercaptoethanol and 100 mM Magnesium Acetate), ATP (5 μM final from a 10 mM stock), polyGluTyr (0.1 mg/mL final from a 1 mg/mL stock), γ-$^{33}$P ATP (10 μCi/μL stock) and water (20 μL/well) was added to each well of a Streptavidin Flashplate.

Test compound in 100% DMSO (0.5 μL) was added to the appropriate wells. Diluted Lyn kinase (human) (Upstate Biotechnology, Lake Placid, N.Y.) (diluted in a buffer consisting of 50 mM Tris at pH 7.5, 0.1 mM EGTA, Sodium Vanadate (0.1 mM), β-mercaptoethanol (0.1%) and 1 mg/mL bovine serum albumin) (2.5 μL) was added to the wells to initiate the reactions.

The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

Percent inhibition was derived according to the procedure described in Example 2. The IC$_{50}$ results for Lyn are shown in Table 5. For those compounds without an IC$_{50}$, the percent inhibition results are shown at a test concentration of 2 μM.

TABLE 5

Lyn IC$_{50}$ (μM)

| Cpd | IC$_{50}$ (avg) |
|---|---|
| 2 | 2.99 |
| 3 | 2% |
| 4 | 0.477 |
| 5 | 83% |
| 6 | 75% |
| 7 | 43% |
| 8 | 40% |
| 9 | 58% |
| 10 | 0.268 |
| 11 | 0.113 |
| 12 | 93% |
| 13 | 76% |
| 18 | 86% |

Example 6 c-Abl Kinase Assay

A mixture of a 10× kinase buffer (80 mM MOPS at pH 7.0, 2 mM EDTA and 100 mM Magnesium Acetate), ATP (5 μM final from a 10 mM stock), a peptide EAIYAAPFAKKK (50 μM final from a 0.5 mM stock), γ-$^{33}$P ATP (10 μCi/μL stock) and water is added to each well (20 μL/well) of a Streptavidin Flashplate.

Test compound in 100% DMSO (0.5 μL) is added to the appropriate wells. Diluted c-Abl kinase (human) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%) and 1 mg/ml bovine serum albumin) (2.5 μL) is added to the wells to initiate the reactions.

The reaction plates are incubated at 30° C. for 40 min. The reaction is terminated by the addition of a 3% phosphoric acid solution (5 μL). The reaction product (10 μL) is spotted onto a P30 filtermat and is washed for 5 minutes in phosphoric acid (75 mM). The wash sequence is repeated two more times and is followed with one final wash in methanol. The plates are then dried, sealed and read on the TopCount scintillation counter after 30 μL scintillation fluid is added. The IC$_{50}$ is derived according to the procedure described in Example 2.

Example 7

Cell Proliferation Inhibition Assay

The ability of a test compound to inhibit unregulated cell proliferation was determined by measuring incorporation of $^{14}$C-labelled thymidine into newly synthesized DNA within cell lines derived from carcinomas originating from several tissues. Accordingly, the anti-proliferative effect of a compound on cells with a variety of phenotypes may be determined.

Carcinoma cell lines include those such as HeLa cervical adenocarcinoma (American Type Culture Collection (ATCC), Virginia, Cat. #CCL-2), A375 malignant melanoma (ATCC CRL-1619), SK-OV-3 ovarian adenocarcinoma (ATCC HTB-77), HCT-116 colon carcinoma (CCL-247), PC-3 prostate adenocarcinoma (ATCC CRL-1435), and MDA-MB-231 (Xenogen Corp.)

The carcinoma cells were trypsinized and counted. The cells (3000-8000 count) were added to each well of a 96-well CytoStar tissue culture treated scintillating microplate (Amersham #RPNQ0160) in complete medium (100 μL) and the plate was then incubated in complete medium for 24 hrs at 37° C. in an inert atmosphere containing 5% $CO_2$. Test compound (1 μL) in 100% DMSO was added to the plate test-wells with DMSO only added to control-wells. The plate was incubated in complete medium for a second 24 hr period at 37° C. in an atmosphere containing 5% $CO_2$.

An aliquot of a solution of Methyl $^{14}$C-thymidine (56 mC/mmol) (NEN #NEC568 or Amersham #CFA532) and complete medium (20 uL to provide 0.2 μCi/well) was then added to each well and the plate was incubated for a third 24 hr period at 37° C. in an atmosphere containing 5% $CO_2$. The plate contents were then discarded, the plate was washed twice with PBS (200 μL) and then PBS (200 μL) was added to each well. The plate was sealed and the degree of methyl $^{14}C$-thymidine incorporation was quantified on a Packard Top Count.

TABLE 6

| | Cell Proliferation IC$_{50}$ (avg, μM) | | |
|---|---|---|---|
| Cpd | A375 | HCT116 | HeLa |
| 41 | >100 | >10 | >100 |
| 42 | >100 | >100 | >100 |
| 45 | >10 | >10 | >100 |
| 46 | >10 | >10 | >10 |
| 48 | 8.29 | 15.8 | >10 |
| 49 | 1.38 | 0.985 | 2.19 |

Example 8

In Vivo Models—Inhibition of Tumor Growth

The ability of a test compound to inhibit unregulated growth of human tumor cells in vivo may be evaluated by implanting human tumor cells into the hindflank of athymic mice, administering a test compound and then quantifying any change in tumor size.

Human epidermoid A431 carcinoma cells ($10^6$ count) are implanted subcutaneously into the hindflank of female athymic mice (Charles River) and allowed to grow for 6-10 days. After a measurable tumor is established (as determined by baseline caliper measurement), the animal is administered an oral dose of the test compound (in 10% solutol) daily for a period of 30 days. Tumor size is measured every five days and the degree of inhibition is determined by comparing drug-treated animals to vehicle-treated animals.

Variations of this method are intended to include intraperitoneal injection or intravenous infusion as the route of administration and administration of the test compound either alone or in a combination therapy.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of Formula (I)

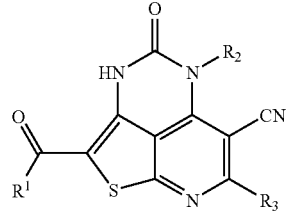

wherein
$R_1$ is selected from the group consisting of —N(Ra,Rb), —O(Ra) and —N(Ra)—(CH$_2$)$_p$—Ar$^1$;

Ra is selected from the group consisting of hydrogen and $C_{1-8}$alkyl;

Rb is selected from the group consisting of hydrogen, $C_{1-8}$alkyl and hydroxy-($C_{1-8}$)alkyl;

alternatively, when $R_1$ is —N(Ra,Rb), then Ra and Rb may be taken together with the nitrogen of attachment to form a heterocyclyl ring having at least one said nitrogen atom, wherein said ring is optionally substituted with one, two or three substituents each selected from the group consisting of $C_{1-8}$alkyl, $C_{2-8}$alkenyl, $C_{2-8}$alkynyl, $C_{1-8}$alkoxy, halogen, hydroxy, hydroxy-($C_{1-8}$)alkyl, hydroxy-($C_{1-8}$)alkoxy, amino and $C_{1-8}$alkyl-amino;

p is 0, 1, 2, 3 or 4;

Ar$^1$ is selected from the group consisting of aryl, heteroaryl, benzofused heteroaryl, heterocyclyl and benzofused heterocyclyl each optionally substituted with one, two or three substituents each selected from the group consisting of $R_4$—($C_{1-8}$)alkyl, $R_4$—($C_{2-8}$)alkenyl, $R_4$—($C_{2-8}$)alkynyl, $R_4$—($C_{1-8}$)alkoxy, cyano, halogen, nitro, halo-($C_{1-8}$)alkyl, halo-($C_{1-8}$)alkoxy, hydroxy, hydroxy-($C_{1-8}$)alkyl, hydroxy-($C_{1-8}$)alkoxy, $C_{1-8}$alkoxy-carbonyl, $C_{1-8}$alkoxy-carbonyl-amino, amino-($C_{1-8}$)alkyl, $C_{1-8}$alkyl-amino-($C_{1-8}$)alkyl, amino, $C_{1-8}$alkyl-amino, $C_{3-8}$cycloalkyl-amino, heterocyclyl-amino (optionally substituted on heterocyclyl with one or two $C_{1-8}$alkyl substituents) and heterocyclyl-($C_{1-8}$)alkyl-amino (optionally substituted on heterocyclyl with one or two $C_{1-8}$alkyl substituents);

$R_4$ is hydrogen or is one, two or three substituents each selected from the group consisting of $C_{3-8}$cycloalkyl, aryl, heteroaryl and heterocyclyl each optionally substituted with one, two or three substituents each selected from the group consisting of $C_{1-8}$alkyl, $C_{1-8}$alkoxy, $C_{1-8}$alkoxy-($C_{1-8}$)alkyl, cyano, halogen, hydroxy, halo-($C_{1-8}$)alkyl, halo-($C_{1-8}$)alkoxy, hydroxy-($C_{1-8}$)alkyl, hydroxy-($C_{1-8}$)alkoxy, $C_{1-8}$alkoxy-carbonyl, amino-($C_{1-8}$)alkyl, $C_{1-8}$alkyl-amino-($C_{1-8}$)alkyl, amino, $C_{1-8}$alkyl-amino, $C_{1-8}$alkoxy-carbonyl-amino;

$R_2$ is selected from the group consisting of aryl, heteroaryl, benzofused heteroaryl, heterocyclyl and benzofused heterocyclyl each optionally substituted with one, two or three substituents each selected from the group consisting of $C_{1-8}$alkyl, $C_{2-8}$alkenyl, $C_{2-8}$alkynyl, $C_{1-8}$alkoxy, cyano, halogen, halo-($C_{1-8}$)alkyl, halo-($C_{1-8}$)alkoxy, hydroxy, heteroaryl-oxy, aryl-oxy (optionally substituted on heteroaryl and aryl with one, two or three substituents each selected from the group consisting of $C_{1-8}$alkyl, $C_{1-8}$alkoxy and halogen); and $R_3$ is hydrogen or is selected from the group consisting of $R_4$—$(C_{1-8})$alkyl, $R_4$—$(C_{2-8})$alkenyl, $R_4$—$(C_{2-8})$alkynyl, halogen, hydroxy, $C_3$-cycloalkyl, heteroaryl, aryl and heterocyclyl, optionally substituted on heteroaryl and aryl with one, two or three substituents each selected from the group consisting of $C_{1-8}$alkyl, $C_{1-8}$alkoxy and halogen.

2. The compound of claim 1, wherein $R_1$ is —N(Ra,Rb).

3. The compound of claim 1, wherein $R_1$ is —O(Ra).

4. The compound of claim 1, wherein when $R_1$ is —N(Ra, Rb), then Ra and Rb may be taken together with the nitrogen of attachment to form a heterocyclyl ring having at least one said nitrogen atom, wherein said ring is optionally substituted with one substituent selected from the group consisting of $C_{1-8}$alkyl, halogen, hydroxy, hydroxy-$(C_{1-8})$alkyl, amino and $C_{1-8}$alkyl-amino.

5. The compound of claim 1, wherein p is 0, 1 or 2.

6. The compound of claim 1, wherein $Ar^1$ is selected from the group consisting of aryl, heteroaryl and heterocyclyl each optionally substituted with one or two substituents each selected from the group consisting of $R_4$—$(C_{1-8})$alkyl, $R_4$—$(C_{1-8})$alkoxy, cyano, halogen, nitro, halo-$(C_{1-8})$alkyl, halo-$(C_{1-8})$alkoxy, hydroxy, hydroxy-$(C_{1-8})$alkyl, hydroxy-$(C_{1-8})$alkoxy, $C_{1-8}$alkoxy-carbonyl, $C_{1-8}$alkoxy-carbonyl-amino, amino-$(C_{1-8})$alkyl, $C_{1-8}$alkyl-amino-$(C_{1-8})$alkyl, amino, $C_{1-8}$alkyl-amino and heterocyclyl-$(C_{1-8})$alkyl-amino.

7. The compound of claim 1, wherein $Ar^1$ is selected from the group consisting of aryl, heteroaryl and heterocyclyl each optionally substituted with one or two substituents each selected from the group consisting of $R_4$—$(C_{1-8})$alkyl, $R_4$—$(C_{1-8})$alkoxy, $C_{1-8}$alkyl-amino and heterocyclyl-$(C_{1-8})$alkyl-amino.

8. The compound of claim 1, wherein $R_4$ is hydrogen or is one, two or three substituents each selected from the group consisting of aryl, heteroaryl and heterocyclyl each optionally substituted with one or two substituents each selected from the group consisting of $C_{1-8}$alkyl, $C_{1-8}$alkoxy, halogen, hydroxy, halo-$(C_{1-8})$alkyl, halo-$(C_{1-8})$alkoxy, hydroxy-$(C_{1-8})$alkyl, hydroxy-$(C_{1-8})$alkoxy, amino-$(C_{1-8})$alkyl, $C_{1-8}$alkyl-amino-$(C_{1-8})$alkyl, amino, $C_{1-8}$alkyl-amino and $C_{1-8}$alkoxy-carbonyl-amino.

9. The compound of claim 1, wherein $R_4$ is hydrogen or is heterocyclyl optionally substituted with one or two substituents each selected from the group consisting of $C_{1-8}$alkyl, $C_{1-8}$alkoxy, halogen, hydroxy, hydroxy-$(C_{1-8})$alkyl, amino, $C_{1-8}$alkyl-amino and $C_{1-8}$alkoxy-carbonyl-amino.

10. The compound of claim 1, wherein $Ar^1$ is selected from the group consisting of aryl, heteroaryl and heterocyclyl each optionally substituted with one or two substituents each selected from the group consisting of $R_4$—$(C_{1-8})$alkyl, $R_4$—$(C_{1-8})$alkoxy, cyano, halogen, nitro, halo-$(C_{1-8})$alkyl, halo-$(C_{1-8})$alkoxy, hydroxy, hydroxy-$(C_{1-8})$alkyl, hydroxy-$(C_{1-8})$alkoxy, $C_{1-8}$alkoxy-carbonyl, $C_{1-8}$alkoxy-carbonyl-amino, amino-$(C_{1-8})$alkyl, $C_{1-8}$alkyl-amino-$(C_{1-8})$alkyl, amino, $C_{1-8}$alkyl-amino and heterocyclyl-$(C_{1-8})$alkyl-amino; and $R_4$ is hydrogen or is one, two or three substituents each selected from the group consisting of aryl, heteroaryl and heterocyclyl each optionally substituted with one or two substituents each selected from the group consisting of $C_{1-8}$alkyl, $C_{1-8}$alkoxy, halogen, hydroxy, halo-$(C_{1-8})$alkyl, halo-$(C_{1-8})$alkoxy, hydroxy-$(C_{1-8})$alkyl, hydroxy-$(C_{1-8})$alkoxy, amino-$(C_{1-8})$alkyl, $C_{1-8}$alkyl-amino-$(C_{1-8})$alkyl, amino, $C_{1-8}$alkyl-amino and $C_{1-8}$alkoxy-carbonyl-amino.

11. The compound of claim 1, wherein $Ar^1$ is selected from the group consisting of aryl, heteroaryl and heterocyclyl each optionally substituted with one or two substituents each selected from the group consisting of $R_4$—$(C_{1-8})$alkyl, $R_4$—$(C_{1-8})$alkoxy, $C_{1-8}$alkyl-amino and heterocyclyl-$(C_{1-8})$alkyl-amino; and $R_4$ is hydrogen or is heterocyclyl optionally substituted with one or two substituents each selected from the group consisting of $C_{1-8}$alkyl, $C_{1-8}$alkoxy, halogen, hydroxy, hydroxy-$(C_{1-8})$alkyl, amino, $C_{1-8}$alkyl-amino and $C_{1-8}$alkoxy-carbonyl-amino.

12. The compound of claim 1, wherein $R_2$ is selected from the group consisting of aryl, heteroaryl and benzofused heterocyclyl each optionally substituted with one, two or three substituents each selected from the group consisting of $C_{1-8}$alkyl, $C_{1-8}$alkoxy, halogen, halo-$(C_{1-8})$alkyl, halo-$(C_{1-8})$alkoxy, heteroaryl-oxy, aryl-oxy (optionally substituted on heteroaryl and aryl with one, two or three substituents each selected from the group consisting of $C_{1-8}$alkyl, $C_{1-8}$alkoxy and halogen).

13. The compound of claim 1, wherein $R_2$ is selected from the group consisting of aryl, heteroaryl and benzofused heterocyclyl each optionally substituted with one, two or three substituents each selected from the group consisting of $C_{1-8}$alkoxy, halogen and aryl-oxy.

14. The compound of claim 1, wherein $R_3$ is hydrogen or is selected from the group consisting of $R_4$—$(C_{1-8})$alkyl, $R_4$—$(C_{2-8})$alkenyl, $R_4$—$(C_{2-8})$alkynyl, halogen, hydroxy, $C_3$-cycloalkyl, heteroaryl, aryl and heterocyclyl, optionally substituted on heteroaryl and aryl with one, two or three substituents each selected from the group consisting of $C_{1-8}$alkyl, $C_{1-8}$alkoxy and halogen.

15. The compound of claim 1, wherein $R_3$ is hydrogen or is selected from the group consisting of $C_{1-8}$alkyl, halogen, hydroxy, aryl and heterocyclyl, optionally substituted on aryl with one or two halogen substituents.

16. The compound of claim 1, wherein $R_1$ is selected from $OCH_2CH_3$, NH-(4-$CH_2$-piperidin-1-yl)-phenyl, NH-(4-$CH_2$-morpholin-4-yl)-phenyl, NH-[4-$(CH_2)_2$-morpholin-4-yl]-phenyl, NH-(1-$CH_3$)-piperidin-4-yl, NH-[4-$(CH_2)_2$-piperidin-1-yl]-phenyl, NH-[4-$(CH_2)_2$-(4-$CH_3$-piperazin-1-yl)]-phenyl, NH-$(CH_2)_2$-pyrrolidin-1-yl, NH-[4-$CH_2$-(4-$OCH_3$-piperidin-1-yl)]-phenyl, NH-[4-$CH_2$-(4-$CH_3$-piperidin-1-yl)]-phenyl, NH-[4-$CH_2$-(3-$CH_2$OH-piperidin-1-yl)]-phenyl, 3-$CH_2$OH-piperidin-1-yl, NH-[4-$CH_2$-(4-$CH_2$OH-piperidin-1-yl)]-phenyl, NH-[4-$CH_2$-(4-OH-piperidin-1-yl)]-phenyl, NH-{4-$CH_2$-[3,5-$(CH_3)_2$-morpholin-4-yl]}-phenyl, NH-{4-$CH_2$-[2,6-cis-$(CH_3)_2$-morpholin-4-yl]}-phenyl, NH-[4-$CH_2$-(4-F-piperidin-1-yl)]-phenyl, NH-[3-N$(CH_3)_2$-4-$CH_2$-morpholin-4-yl]-phenyl, 4-OH-piperidin-1-yl, N$(CH_3)$-(4-$CH_2$-morpholin-4-yl)-phenyl, NH-[6-NH$(CH_2)_3$-morpholin-4-yl]-pyridin-3-yl, NH-[3-$OCH_3$-4-O$(CH_2)_2$-piperidin-1-yl]-phenyl, NH-[4-$OCH_3$-(1-$CH_3$-piperidin-2-yl)]-phenyl, NH-pyrazol-3-yl, NH-(5-$CH_3$)-isoxazol-3-yl, NH-pyrimidin-2-yl, NH-pyridin-3-yl, NH-pyridin-2-yl, NH-C$(CH_3)_2$$CH_2$OH, NH-(1-$CH_3$)-pyrazol-3-yl, NH-pyridin-4-yl, 4-N$(CH_3)_2$-piperidin-1-yl, NH-{4-$CH_2$-[4-N$(CH_3)_2$-piperidin-1-yl]}-phenyl, 3-F-piperidin-1-yl, NH-[4-$CH_2$-(3-F-piperidin-1-yl)]-phenyl, NH-[3-$OCH_3$-4-$CH_2$-morpholin-4-yl]-phenyl, NH-{4-$CH_2$-[4-NHC(O)OC$(CH_3)_3$-piperidin-1-yl]}-phenyl, NH-[4-$CH_2$-(4-$NH_2$-piperidin-1-yl)]-phenyl or NH-[4-$CH_2$-(4,4-$F_2$-piperidin-1-yl)]-phenyl;

R₂ is selected from 3-Cl-phenyl, 2,4-Cl₂-5-OCH₃-phenyl, pyridin-4-yl, 4-phenoxy-phenyl or 5-Cl-benzo[1,3]dioxol-4-yl; and R₃ is selected from hydrogen, OH, Cl, morpholin-4-yl, CH₃ or 2-Cl-5-F-phenyl.

17. The compound of claim 1, selected from:

5-(2-chloro-phenyl)-6-cyano-4-oxo-4,5-dihydro-3H-1-thia-3,5,8-triaza-acenaphthylene-2-carboxylic acid (4-morpholin-4-ylmethyl-phenyl)-amide, 5-(5-chloro-benzo[1,3]dioxol-4-yl)-6-cyano-4-oxo-4,5-dihydro-3H-1-thia-3,5,8-triaza-acenaphthylene-2-carboxylic acid (4-morpholin-4-ylmethyl-phenyl)-amide, 6-cyano-5-(2,4-dichloro-5-methoxy-phenyl)-4-oxo-4,5-dihydro-3H-1-thia-3,5,8-triaza-acenaphthylene-2-carboxylic acid (4-morpholin-4-ylmethyl-phenyl)-amide, 6-cyano-5-(2,4-dichloro-5-methoxy-phenyl)-4-oxo-4,5-dihydro-3H-1-thia-3,5,8-triaza-acenaphthylene-2-carboxylic acid [4-(2-morpholin-4-yl-ethyl)-phenyl]-amide, 5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid ethyl ester, 5-(5-chloro-benzo[1,3]dioxol-4-yl)-6-cyano-7-morpholin-4-yl-4-oxo-4,5-dihydro-3H-1-thia-3,5,8-triaza-acenaphthylene-2-carboxylic acid (4-morpholin-4-ylmethyl-phenyl)-amide, 5-(5-chloro-benzo[1,3]dioxol-4-yl)-6-cyano-7-methyl-4-oxo-4,5-dihydro-3H-1-thia-3,5,8-triaza-acenaphthylene-2-carboxylic acid (4-morpholin-4-ylmethyl-phenyl)-amide, 5-(5-chloro-benzo[1,3]dioxol-4-yl)-6-cyano-4-oxo-4,5-dihydro-3H-1-thia-3,5,8-triaza-acenaphthylene-2-carboxylic acid (1-methyl-piperidin-4-yl)-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(2-piperidin-1-yl-ethyl)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid {4-[2-(4-methyl-piperazin-1-yl)-ethyl]-phenyl}-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methoxy-piperidin-1-ylmethyl)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-methyl-piperidin-1-ylmethyl)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(3-hydroxymethyl-piperidin-1-ylmethyl)-phenyl]-amide, 5-(5-chloro-benzo[1,3]dioxol-4-yl)-2-(3-hydroxymethyl-piperidine-1-carbonyl)-4-oxo-4,5-dihydro-3H-1-thia-3,5,8-triaza-acenaphthylene-6-carbonitrile, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxymethyl-piperidin-1-ylmethyl)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-hydroxy-piperidin-1-ylmethyl)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid (3-dimethylamino-4-morpholin-4-ylmethyl-phenyl)-amide, 5-(5-chloro-benzo[1,3]dioxol-4-yl)-2-(4-hydroxy-piperidine-1-carbonyl)-4-oxo-4,5-dihydro-3H-1-thia-3,5,8-triaza-acenaphthylene-6-carbonitrile, 5-(5-chloro-benzo[1,3]dioxol-4-yl)-6-cyano-4-oxo-4,5-dihydro-3H-1-thia-3,5,8-triaza-acenaphthylene-2-carboxylic acid [6-(3-morpholin-4-yl-propylamino)-pyridin-3-yl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [3-methoxy-4-(2-piperidin-1-yl-ethoxy)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(1-methyl-piperidin-2-ylmethoxy)-phenyl]-amide, 5-(5-chloro-benzo[1,3]dioxol-4-yl)-6-cyano-4-oxo-4,5-dihydro-3H-1-thia-3,5,8-triaza-acenaphthylene-2-carboxylic acid (1H-pyrazol-3-yl)-amide, 5-(5-chloro-benzo[1,3]dioxol-4-yl)-6-cyano-4-oxo-4,5-dihydro-3H-1-thia-3,5,8-triaza-acenaphthylene-2-carboxylic acid (5-methyl-isoxazol-3-yl)-amide, 5-(5-chloro-benzo[1,3]dioxol-4-yl)-6-cyano-4-oxo-4,5-dihydro-3H-1-thia-3,5,8-triaza-acenaphthylene-2-carboxylic acid pyrimidin-2-ylamide, 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-3-ylamide, 5-(5-chloro-benzo[1,3]dioxol-4-yl)-6-cyano-4-oxo-4,5-dihydro-3H-1-thia-3,5,8-triaza-acenaphthylene-2-carboxylic acid pyridin-4-ylamide, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-dimethylamino-piperidin-1-ylmethyl)-phenyl]-amide, 6-cyano-4-oxo-5-(4-phenoxy-phenyl)-4,5-dihydro-3H-1-thia-3,5,8-triaza-acenaphthylene-2-carboxylic acid (3-methoxy-4-morpholin-4-ylmethyl-phenyl)-amide,

[1-(4-{[5-(5-chloro-benzo[1,3]dioxol-4-yl)-6-cyano-4-oxo-4,5-dihydro-3H-1-thia-3,5,8-triaza-acenaphthylene-2-carbonyl]-amino}-benzyl)-piperidin-4-yl]-carbamic acid tert-butyl ester, 5-(5-chloro-benzo[1,3]dioxol-4-yl)-6-cyano-4-oxo-4,5-dihydro-3H-1-thia-3,5,8-triaza-acenaphthylene-2-carboxylic acid [4-(4-amino-piperidin-1-ylmethyl)-phenyl]-amide, 6-cyano-4-oxo-5-(4-phenoxy-phenyl)-4,5-dihydro-3H-1-thia-3,5,8-triaza-acenaphthylene-2-carboxylic acid [4-(2-piperidin-1-yl-ethyl)-phenyl]-amide, 6-cyano-4-oxo-5-(4-phenoxy-phenyl)-4,5-dihydro-3H-1-thia-3,5,8-triaza-acenaphthylene-2-carboxylic acid (4-piperidin-1-ylmethyl-phenyl)-amide, 6-cyano-4-oxo-5-(4-phenoxy-phenyl)-4,5-dihydro-3H-1-thia-3,5,8-triaza-acenaphthylene-2-carboxylic acid (4-morpholin-4-ylmethyl-phenyl)-amide, 6-cyano-4-oxo-5-(4-phenoxy-phenyl)-4,5-dihydro-3H-1-thia-3,5,8-triaza-acenaphthylene-2-carboxylic acid [4-(4-methoxy-piperidin-1-ylmethyl)-phenyl]-amide, or 6-cyano-7-hydroxy-4-oxo-5-(4-phenoxy-phenyl)-4,5-dihydro-3H-1-thia-3,5,8-triaza-acenaphthylene-2-carboxylic acid ethyl ester.

18. A pharmaceutical composition comprising an effective amount of the compound of claim 1.

19. The pharmaceutical composition of claim 18, wherein the effective amount of the compound is in a range of from about 0.001 mg/kg to about 300 mg/kg of body weight per day.

* * * * *